US012053444B2

(12) United States Patent
Alibhai et al.

(10) Patent No.: US 12,053,444 B2
(45) Date of Patent: *Aug. 6, 2024

(54) THERAPEUTIC COMPOUNDS, FORMULATIONS, AND USES THEREOF

(71) Applicant: Tvardi Therapeutics, Inc., Sugar Land, TX (US)

(72) Inventors: Imran Alibhai, Sugar Land, TX (US); Sofia de Achaval, Missouri City, TX (US); Beverly C. Langevin, Stewartsville, NJ (US); Tian Zhou, Philadelphia, PA (US)

(73) Assignee: Tvardi Therapeutics, Inc., Sugar Land, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/059,270

(22) Filed: Nov. 28, 2022

(65) Prior Publication Data

US 2023/0285334 A1 Sep. 14, 2023

Related U.S. Application Data

(63) Continuation of application No. 17/305,009, filed on Jun. 29, 2021, now Pat. No. 11,547,683, which is a continuation of application No. 17/203,639, filed on Mar. 16, 2021, now Pat. No. 11,077,077, which is a continuation of application No. PCT/US2021/014642, filed on Jan. 22, 2021.

(60) Provisional application No. 62/965,738, filed on Jan. 24, 2020.

(51) Int. Cl.
*A61K 31/18* (2006.01)
*A61K 9/00* (2006.01)
*A61K 9/48* (2006.01)

(52) U.S. Cl.
CPC ............ *A61K 31/18* (2013.01); *A61K 9/0053* (2013.01); *A61K 9/4825* (2013.01); *A61K 9/4858* (2013.01); *A61K 9/4866* (2013.01); *A61K 9/4875* (2013.01)

(58) Field of Classification Search
CPC .... A61K 31/18; A61K 9/0053; A61K 9/4825; A61K 9/4858; A61K 9/4866; A61K 9/4875; A61K 9/1075; A61K 9/1635; A61K 9/5138; A61K 47/10; A61K 47/26; A61K 47/44; A61K 31/167; Y02A 50/30; A61P 29/00; A61P 35/00; A61P 43/00; C07C 311/29; C07B 2200/13
See application file for complete search history.

(56) References Cited

U.S. PATENT DOCUMENTS

| | | |
|---|---|---|
| 4,279,909 A | 7/1981 | Takashima |
| 6,492,428 B1 | 12/2002 | Al-Abed et al. |
| 6,608,101 B1 | 8/2003 | Ni et al. |
| 8,779,001 B2 | 7/2014 | Tweardy et al. |
| 8,975,399 B2 | 3/2015 | Zagury et al. |
| 10,112,933 B2 | 10/2018 | Tweardy et al. |
| 10,676,455 B2 | 6/2020 | Tweardy et al. |
| 11,026,905 B2 | 6/2021 | De Achaval et al. |
| 11,077,077 B1 | 8/2021 | Alibhai et al. |
| 11,161,831 B2 | 11/2021 | Tweardy et al. |
| 11,547,683 B2 | 1/2023 | Alibhai et al. |
| 2004/0048795 A1 | 3/2004 | Ivanova et al. |
| 2005/0239886 A1 | 10/2005 | Hamuro et al. |
| 2005/0287664 A1 | 12/2005 | Fann |
| 2006/0148715 A1 | 7/2006 | Tweardy |
| 2006/0239990 A1 | 10/2006 | Nabel et al. |
| 2007/0004704 A1 | 1/2007 | Damon et al. |
| 2007/0203236 A1 | 8/2007 | Smith et al. |
| 2009/0221542 A1 | 9/2009 | Wang et al. |
| 2009/0326063 A1 | 12/2009 | Sporn et al. |
| 2010/0035793 A1 | 2/2010 | Lim et al. |
| 2010/0041685 A1 | 2/2010 | Tweardy et al. |
| 2010/0209950 A1 | 8/2010 | Gernez et al. |
| 2010/0292234 A1 | 11/2010 | Pettus et al. |
| 2011/0312984 A1 | 12/2011 | Tweardy et al. |
| 2012/0003191 A1 | 1/2012 | Burkin et al. |
| 2012/0035163 A1 | 2/2012 | Yasuma et al. |
| 2012/0040917 A1 | 2/2012 | Orum et al. |
| 2012/0178718 A1 | 7/2012 | Nique et al. |
| 2012/0308564 A1 | 12/2012 | Bayliffe |
| 2013/0022993 A1 | 1/2013 | Doi et al. |
| 2013/0123266 A1 | 5/2013 | Zagury et al. |
| 2014/0088171 A1 | 3/2014 | Yan et al. |

(Continued)

FOREIGN PATENT DOCUMENTS

| | | |
|---|---|---|
| CA | 2805206 A1 | 2/2012 |
| WO | WO-2007136858 A2 | 11/2007 |

(Continued)

OTHER PUBLICATIONS

Strickley, R.G. Solubilizing excipients in oral and injectable formulations. Pharmaceutical Research, vol. 21, No. 2. (Year: 2004).*
Bharadwaj, U., et al., Small-molecule inhibition of STAT3 in radioresistant head and neck squamous cell carcinoma, Oncotarget, 7(18): 26307-26330 (2016).
Bonetto, A., et al., STAT3 activation in skeletal muscle links muscle wasting and the acute phase response in cancer cachexia, PLoS One, 6(7): e22538 (2011).
De Castro Barbosa, T., et al., Potential Role of Growth Hormone in Impairment of Insulin Signaling in Skeletal Muscle, Adipose Tissue, and Liver of Rats Chronically Treated with Arginine, Endocrinology, 150(5): 2080-2086 (2009).

(Continued)

*Primary Examiner* — Jessica Worsham
(74) *Attorney, Agent, or Firm* — Goodwin Procter LLP

(57) ABSTRACT

Provided herein are compositions, formulations, and (e.g., oral) dosage forms comprising a compound of Formula (I). In specific instances, such compositions comprise an emulsifier, a solubilizer, a polyethylene glycol, a surfactant, and an antioxidant. In some instances, such compositions are useful for the treatment of fibrosis, cancer, and/or chronic inflammation.

20 Claims, 8 Drawing Sheets

(56) References Cited

U.S. PATENT DOCUMENTS

| | | | |
|---|---|---|---|
| 2014/0296270 A1 | 10/2014 | Tweardy et al. | |
| 2015/0024032 A1* | 1/2015 | Tweardy | A61K 31/4196 546/172 |
| 2015/0031714 A1 | 1/2015 | Tweardy et al. | |
| 2015/0038443 A1 | 2/2015 | Li et al. | |
| 2015/0045358 A1 | 2/2015 | Kao et al. | |
| 2018/0009839 A1 | 1/2018 | Anderson et al. | |
| 2020/0331880 A1 | 10/2020 | Tweardy et al. | |
| 2021/0114980 A1 | 4/2021 | Wied et al. | |
| 2021/0322347 A1 | 10/2021 | Alibhai et al. | |
| 2022/0227750 A1 | 7/2022 | Tweardy et al. | |
| 2023/0077280 A1 | 3/2023 | Mitch et al. | |

FOREIGN PATENT DOCUMENTS

| | | |
|---|---|---|
| WO | WO-2009149192 A1 | 12/2009 |
| WO | WO-2012017166 A2 | 2/2012 |
| WO | WO-2013020372 A1 | 2/2013 |
| WO | WO-2013078372 A1 | 5/2013 |
| WO | WO-2015010106 A1 | 1/2015 |
| WO | WO-2015010107 A1 | 1/2015 |
| WO | WO-2019204614 A1 | 10/2019 |
| WO | WO-2021113551 A1 | 6/2021 |

OTHER PUBLICATIONS

Kim, J-H., et al., Signal Transducer and Activator of Transcription 3 (STAT3) Mediates Amino Acid Inhibition of Insulin Signaling through Serine 727 Phosphorylation, J Biol Chem, 284(51): 35425-35432 (2009).

Mashili, F., et al., Constitutive STAT3 Phosphorylation Contributes to Skeletal Muscle Insulin Resistance in Type 2 Diabetes, Diabetes, 62(2): 457-465 (2013).

Santos Silva, K.A., et al., Inhibition of Stat3 activation suppresses caspase-3 and the ubiquitin-proteasome system, leading to preservation of muscle mass in cancer cachexia, J Biol Chem, 290(17): 11177-11187 (2015).

White, A.T., et al., Knockout of STAT3 in skeletal muscle does not prevent high-fat diet-induced insulin resistance, Mol Metab, 4(8): 569-575 (2015).

Zhang, L., et al., IL-6 and serum amyloid A synergy mediates angiotensin II-induced muscle wasting, J Am Soc Nephrol, 20(3): 604-612 (2009).

Zhang, L., et al., Stat3 activation links a C/EBPδ to myostatin pathway to stimulate loss of muscle mass, Cell Metab, 18(3): 368-379 (2013).

Zhang, L., Pharmacological inhibition of myostatin suppresses systemic inflammation and muscle atrophy in mice with chronic kidney disease, FASEB J, 25(5): 1653-1663 (2011).

Zhang, L., Satellite cell dysfunction and impaired IGF-1 signaling cause CKD-induced muscle atrophy, J Am Soc Nephrol, 21(3): 419-427 (2010).

Avery, D.T., et al., "STAT3 is required for IL-21-induced secretion of IgE from human naive B cells", BLOOD, 112(5): 1784-1793 (Sep. 1, 2008).

Choi, I., et al., "TNF-α induces the late-phase airway hyper-responsiveness and airway inflammation through cytosolic phospholipase A(2) activation", J. Allergy Clin. Immunol., 116:537-543, (Sep. 2005).

Debnath, B., et al., "Small Molecule Inhibitors of Signal Transducer and Activator of Transcription 3 (Stat3) Protein", J. Med. Chem., 55: 6645-6668, (2012).

Fan, D., et al., "Cardic fibroblasts, fibrosis and extracellular matrix remodeling in heart disease", Fibrogenesis & Tissue Repair, 5:15 (2012).

Hakala, M., "Poor prognosis in patients with rheumatoid arthritis hospitalized for interstitial lung fibrosis", Chest, 93:114-118, (1988).

Kang, N., et al., "Tumor Necrosis Factor-alpha Develops Late Anaphylactic Reaction through Cytosolic Phospholipase A(2) Activation", Int. Arch. Allergy Immunol. 147(4): 315-322 (Aug. 2008).

Lindsay, K., et al., "Liver fibrosis in patients with psoriasis and psoriatic arthritis on long-term, high cumulative dose methotrexate therapy", Rheumatology, 48:569-572, (2009).

Mak, R.H., et al., "Wasting in chronic kidney disease", J. Cachexia Sarcopenia Muscle, 2:9-25, (Mar. 2011).

McMurray, U.S., "Structural Basis for the Binding of High Affinity Phosphopeptides to Stat3", PeptideScience, 90(1):69-79, (Nov. 27, 2007).

Morley, J.E., et al., "Cachexia: pathophysiology and clinical relevance", Am J. Clin Nutr., 83(4):735-743, (Apr. 2006).

PCT/US2019/028135 International Search Report and Written Opinion mailed Jul. 5, 2019.

PCT/US2020/063167 International Search Report and Written Opinion dated Mar. 3, 2021.

PCT/US2021/014642 International Preliminary Report on Patentability dated Jul. 26, 2022.

PCT/US2021/014642 International Search Report and Written Opinion mailed Jun. 16, 2021.

Pedroza, M., et al., "Role of STAT3 in skin fibrosis and transforming growth factor beta signalling", Rheumatology, 57: 1838-1850 (2018).

PUBCHEM-CID: 247699, pp. 1-13, (Mar. 26, 2005).

Silva, et al., "A New therapeutical approach to block cancer cachexia: focusing inhibition of STAT3", The FASEB Journal, 27(S1):2 pgs, Abstract (2013).

U.S. Appl. No. 12/477,583 dated May 23, 2013.
U.S. Appl. No. 12/477,583 dated Nov. 9, 2011.
U.S. Appl. No. 12/477,583 Office Action dated Aug. 30, 2012.
U.S. Appl. No. 14/335,804 Office Action dated May 16, 2017.
U.S. Appl. No. 14/335,804 Office Action dated May 17, 2016.
U.S. Appl. No. 14/335,804 Office Action dated May 7, 2015.
U.S. Appl. No. 14/335,804 Office Action dated Oct. 16, 2015.
U.S. Appl. No. 14/335,829 Office Action dated Apr. 13, 2018.
U.S. Appl. No. 14/335,829 Office Action dated Apr. 26, 2021.
U.S. Appl. No. 14/335,829 Office Action dated Feb. 28, 2020.
U.S. Appl. No. 14/335,829 Office Action dated Jan. 5, 2017.
U.S. Appl. No. 14/335,829 Office Action dated Jan. 8, 2021.
U.S. Appl. No. 14/335,829 Office Action dated Jun. 12, 2015.
U.S. Appl. No. 14/335,829 Office Action dated Jun. 19, 2019.
U.S. Appl. No. 14/335,829 Office Action dated May 10, 2017.
U.S. Appl. No. 14/335,829 Office Action dated May 13, 2016.
U.S. Appl. No. 14/335,829 Office Action dated Nov. 4, 2015.
U.S. Appl. No. 14/335,829 Office Action dated Nov. 7, 2018.
U.S. Appl. No. 14/335,829 Office Action dated Oct. 25, 2019.
U.S. Appl. No. 14/335,829 Office Action dated Sep. 22, 2020.
U.S. Appl. No. 14/335,829 Office Action dated Sep. 28, 2021.
U.S. Appl. No. 14/335,853 Office Action dated Feb. 1, 2016.
U.S. Appl. No. 14/335,853 Office Action dated Feb. 5, 2019.
U.S. Appl. No. 14/335,853 Office Action dated Jul. 9, 2019.
U.S. Appl. No. 14/335,853 Office Action dated Mar. 13, 2017.
U.S. Appl. No. 14/335,853 Office Action dated May 17, 2018.
U.S. Appl. No. 14/335,853 Office Action dated Nov. 29, 2019.
U.S. Appl. No. 14/335,853 Office Action dated Oct. 6, 2017.
U.S. Appl. No. 14/335,853 Office Action dated Sep. 29, 2016.
U.S. Appl. No. 16/848,661 Office Action dated Mar. 11, 2021.

Xu, X., et al., "Chemical Probes that Competitively and Selectively Inhibit Stat3 Activation", PLoS One, 4(3): e4783, (Mar. 2009).

* cited by examiner

| Group # | # of Rats | Formulation | Conc (mg/mL) | Pre-Dose Water Dispersion (Formulation:Water) | Concentration of Final Dosing Solution (mg/mL) | Dose Volume (mL/kg) | Dose (mg/kg) |
|---|---|---|---|---|---|---|---|
| 1 | 6 | Labrasol/PEG400 | 2.5 | None | 2.5 | 10 | 25 |
| 2 | 6 | Labrasol/PEG400 | 25 | 1:9 | 2.5 | 10 | 25 |
| 3 | 8 | Formulation D | 25 | 1:9 | 2.5 | 10 | 25 |
| 4 | 6 | Formulation D | 25 | 1:2 | 8.3 | 3 | 25 |

FIG. 4

|  |  | Subject Identifier | | | | | | | | | | | |
|---|---|---|---|---|---|---|---|---|---|---|---|---|---|
|  |  | Cohort 1 (1.6 mg/kg) | | | | Cohort 2 (3.2 mg/kg) | | | Cohort 3 (6.4 mg/kg) | | | | | |
|  |  | 3 | 4 | 6 | 7 | 8 | 9 | 10 | 11 | 12 | 15 | 16 | 19 | 20 |
| Parameter | Units | Estimate | | | | | | | | | | | | |
| Dose | mg | 150 | 210 | 150 | 150 | 360 | 240 | 270 | 450 | 570 | 420 | 480 | 450 | 420 |
| $T_{max}$ | h | 0.817 | 4 | 1 | 1.83 | 2 | 1.08 | 1.08 | 8.08 | 2.08 | 2 | 4.17 | 1.08 | 1 |
| $C_{max}$ | ng/mL | 1030 | 1200 | 1380 | 735 | 2380 | 1910 | 3260 | 2360 | 2800 | 2220 | 3730 | 2330 | 2820 |
| $C_{max}\_D$ | ng/mL/mg | 5.72 | 5.48 | 9.2 | 4.9 | 6.17 | 7.96 | 12.1 | 5.02 | 4.91 | 5.29 | 7.77 | 5.18 | 6.71 |
| $AUC_{inf}$ | h*ng/mL | 5430 | 7640 | 6560 | 5800 | 11700 | 12800 | 19800 | 20400 | 17200 | 21400 | 29200 | 12700 | 14600 |
| $AUC_{inf}\_D$ | h*ng/mL/mg | 30.1 | 34.9 | 43.8 | 38.7 | 32.5 | 53.3 | 73.3 | 45.4 | 30.1 | 50.9 | 60.8 | 28.2 | 34.8 |
| $T_{1/2}$ | h | 6.74 | 6.5 | 5.52 | 13.3 | 5.21 | 3.34 | 8.28 | 12.6 | 12.5 | 12.3 | 28.9 | 7.16 | 3.88 |
| Lambda_z_lower | h | 4 | 4 | 6 | 6 | 6 | 8 | 4 | 6.08 | 4.22 | 4 | 5.93 | 6 | 1 |
| Lambda_z_upper | h | 11.6 | 11.8 | 11.8 | 13.7 | 12 | 11.5 | 11.7 | 11.5 | 11.7 | 11.6 | 11.7 | 11.8 | 11.8 |
| No_points_lambda_z |  | 4 | 4 | 3 | 3 | 3 | 3 | 4 | 3 | 4 | 3 | 3 | 3 | 6 |
| Rsq_adjusted |  | 0.913 | 0.668 | 0.99 | 1 | 0.983 | 0.989 | 0.927 | 0.987 | 0.878 | 0.91 | 0.913 | 0.953 | 0.982 |

FIG. 5

| Parameter | Units | Cohort 1 (1.6 mg/kg) | | | Cohort 2 (3.2 mg/kg) | | | Cohort 3 (6.4 mg/kg) | | |
|---|---|---|---|---|---|---|---|---|---|---|
| | | N | Mean | SD | N | Mean | SD | N | Mean | SD |
| Dose | mg | 4 | 175 | 32.7 | 3 | 290 | 62.4 | 6 | 465 | 56.1 |
| $T_{max}$ | h | 4 | 1.91 | 1.46 | 3 | 1.39 | 0.529 | 6 | 2.74 | 2 |
| $C_{max}$ | ng/mL | 4 | 1090 | 274 | 3 | 2460 | 707 | 6 | 2690 | 575 |
| $C_{max}\_D$ | ng/mL/mg | 4 | 6.33 | 1.93 | 3 | 8.73 | 3.03 | 6 | 5.81 | 1.17 |
| $AUC_{last}$ | h*ng/mL | 4 | 6360 | 976 | 3 | 14800 | 4380 | 6 | 19200 | 5890 |
| $AUC_{last}\_D$ | h*ng/mL/mg | 4 | 36.9 | 5.77 | 3 | 53 | 20.4 | 6 | 41.7 | 12.9 |
| HL_Lambda_z ($T_{1/2}$) | h | 4 | 8.01 | 3.54 | 3 | 5.61 | 2.49 | 6 | 12.9 | 8.61 |
| Lamba_z_lower | h | 4 | 5 | 1.15 | 3 | 5.33 | 1.15 | 6 | 4.54 | 1.97 |
| Lambda_z_upper | h | 4 | 12 | 0.487 | 3 | 11.7 | 0.243 | 6 | 11.7 | 0.119 |
| No_points_lambda_z | | 4 | 3.5 | 0.577 | 3 | 3.33 | 0.577 | 6 | 3.67 | 1.21 |
| Rsq_adjusted | | 4 | 0.891 | 0.153 | 3 | 0.97 | 0.038 | 6 | 0.934 | 0.04 |
| AUC_%Extrap_obs | % | 4 | 34.8 | 12.8 | 3 | 22.9 | 13 | 6 | 47.5 | 23.7 |

FIG. 6

THERAPEUTIC COMPOUNDS, FORMULATIONS, AND USES THEREOF

CROSS-REFERENCE TO RELATED APPLICATIONS

This application is a continuation of U.S. application Ser. No. 17/305,009, filed on Jun. 29, 2021, now issued as U.S. Pat. No. 11,547,683 on Jan. 10, 2023, which is a continuation of U.S. application Ser. No. 17/203,639, filed on Mar. 16, 2021, now issued as U.S. Pat. No. 11,077,077 on Aug. 3, 2021, which is a continuation of International Application No. PCT/US2021/014642, filed on Jan. 22, 2021, which claims the benefit and priority of U.S. Provisional Application No. 62/965,738, filed on Jan. 24, 2020, the contents of each are hereby incorporated by reference in their entireties.

TECHNICAL FIELD

Provided herein is a compound of Formula (I), and pharmaceutical compositions and uses thereof, such as in the treatment of cancer, fibrosis, or chronic inflammation.

BACKGROUND

While great strides have been made in the treatment of cancer, a cure remains elusive. In recent years, advancements in formulation chemistry have increased the range of therapeutic compounds that can be utilized in cancer treatment.

SUMMARY

Provided in some embodiments herein is a compound of Formula (I):

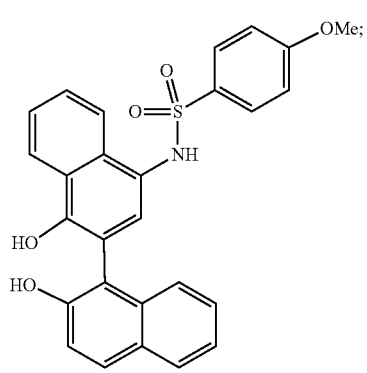

such as for use in therapies for cancer, fibrosis, or chronic inflammation. Provided in certain embodiments are pharmaceutical compositions comprising a compound of Formula (I). In general instances, compounds of Formula (I) have low solubility and are very difficult to formulate in a practical and usable form. For example, in some instances, formulations, such as comprising a combination of Labrasol® and PEG400 (60:40), require unmanageable pill burden at even modest dosing. In certain instances, provided herein are compositions and formulations capable of providing good solubility of a compound of Formula (I) and/or reducing pill burden in therapies involving a compound of Formula (I).

While a compound of Formula (I) is generally considered to be highly insoluble (akin to "brick dust"), in certain instances, compositions and formulations provided herein are able to provide high loading of a compound of Formula (I), good ability to solubilize a compound of Formula (I), good ability to provide for high bioavailability of a compound of Formula (I), good stability (e.g., chemical and/or physical stability), and/or reduce pill burden for individuals receiving therapies involving the administration of a compound of Formula (I).

In some embodiments, a composition, formulation or oral dosage form provided herein comprises, in addition to the compound of Formula (I), any suitable excipient or combination of excipients. In certain embodiments, the formulation (e.g., excipient or combination of excipients thereof) is suitable for providing good solubility of a compound of Formula (I), good physical stability (e.g., good solubility and/or dispersion of a compound of Formula (I)), good chemical stability of a compound of Formula (I), good (e.g., oral) bioavailability of a compound of Formula (I), and/or desirable or therapeutic effect, with a manageable (e.g., fewer than 25 pills per day, or other amount described herein) or reduced pill burden (e.g., relative to two-component excipient systems described herein) and/or an acceptable toxicity profile (e.g., gastrointestinal toxicity profile, such as due at least in part to the low or reduced levels of excipient(s) present in the compositions and formulations provided herein relative to alternative formulations).

Provided in certain embodiments herein are pharmaceutical compositions, formulations, and oral dosage forms comprising an (e.g., therapeutically effective) amount of a compound of Formula (I):

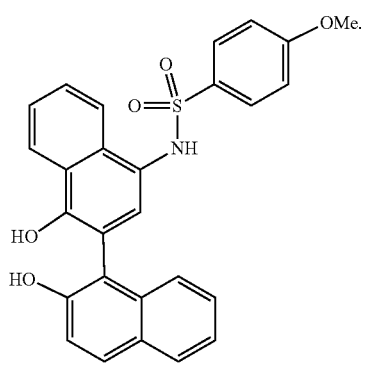

In some embodiments, provided herein, are methods of using a compound of Formula (I), or a composition, formulation, or oral dosage form comprising a compound of Formula (I). In certain embodiments, such methods are methods for providing a therapeutic effect, such as treating a disease or disorder mediated by STAT3, cancer, fibrosis, or chronic inflammation (e.g., with a manageable or reduced pill burden). In some embodiments, methods provided herein comprise administering a compound of Formula (I), or a composition, formulation, or oral dosage form thereof, such as to achieve a certain pharmacokinetic profile, such as described herein.

Provided herein, in one aspect, is a pharmaceutical composition comprising:
a. a therapeutically effective amount of a compound of Formula (I):

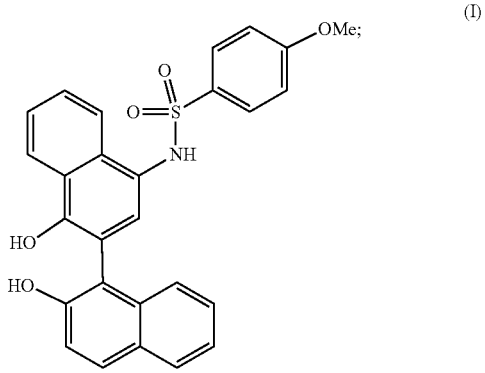 [SMILES: COc1ccc(S(=O)(=O)Nc2cc(-c3c(O)ccc4ccccc34)c(O)c3ccccc23)cc1]

b. an emulsifier (e.g., glyceride), the emulsifier being present in the composition in a weight ratio of compound of Formula (I) to the emulsifier of about 1:1 to about 1:2 (e.g., about 1:1.5);
c. a solubilizer, the solubilizer being present in the composition in a weight ratio of compound of Formula (I) to solubilizer of about 1:1 to about 1:5 (e.g., about 1:2 to about 1:4, e.g., about 1:3);
d. a polyethylene glycol (PEG), the polyethylene glycol being present in the composition in a weight ratio of compound of Formula (I) to polyethylene glycol of about 1:2 to about 1:6 (e.g., about 1:3 to about 1:5, e.g., about 1:4);
e. a surfactant, the surfactant being present in the composition in a weight ratio of compound of Formula (I) to surfactant of about 2:1 to about 1:2 (e.g., about 1:1 to about 1:2, e.g., about 1:1); and
f. an (e.g., optional) antioxidant, the antioxidant being present in the composition in a weight ratio of compound of Formula (I) to antioxidant of about 10:1 to about 30:1 (e.g., about 15:1 to about 25:1, e.g., about 20:1).

Provided herein, in one aspect, is a pharmaceutical composition comprising:
a. a therapeutically effective amount of a compound of Formula (I):

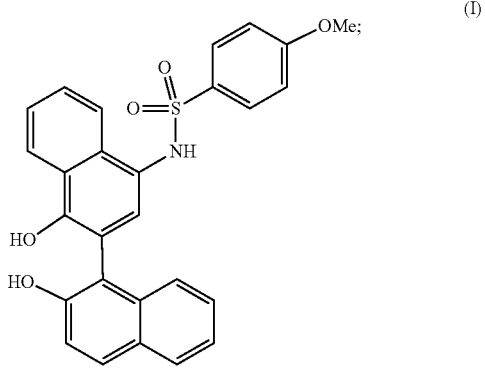 [SMILES: COc1ccc(S(=O)(=O)Nc2cc(-c3c(O)ccc4ccccc34)c(O)c3ccccc23)cc1]

b. an emulsifier (e.g., glyceride), the emulsifier being present in the composition in a weight ratio of compound of Formula (I) to the emulsifier of about 1:3 to about 1:7;
c. a solubilizer, the solubilizer being present in the composition in a weight ratio of compound of Formula (I) to solubilizer of about 1:10 to about 1:20 (e.g., about 1:11 to about 1:16);
d. a polyethylene glycol (PEG), the polyethylene glycol being present in the composition in a weight ratio of compound of Formula (I) to polyethylene glycol of about 1:12 to about 1:20 (e.g., about 1:15 to about 1:17);
e. a surfactant, the surfactant being present in the composition in a weight ratio of compound of Formula (I) to surfactant of about 1:2 to about 1:6 (e.g., about 1:3 to about 1:5);
f. an (e.g., optional) antioxidant, the antioxidant being present in the composition in a weight ratio of compound of Formula (I) to antioxidant of about 2:1 to about 20:1 (e.g., about 5:1).

In certain embodiments, the composition is or is a part of a self-emulsifying drug dispersion (SEDD). In certain embodiments, the composition is a capsule fill formulation. In certain embodiments, the composition further comprises a capsule shell.

In certain embodiments, the compound of Formula (I) is present in the formulation in a concentration of at least 50 mg/g (e.g., at least 60 mg/g, at least 70 mg/g, at least 80 mg/g, or at least 90 mg/g) (e.g., excluding the mass of a capsule shell). In certain embodiments, the compound of Formula (I) is present in the formulation in a concentration of at least 60 mg/mL (e.g., at least 70 mg/mL, at least 80 mg/mL, at least 90 mg/mL, or at least 100 mg/mL) (e.g., excluding the volume of a capsule shell). In certain embodiments, at least 60 wt. % (e.g., at least 80 wt. %, at least 90 wt. %, or at least 95 wt. %) of the compound of Formula (I) is soluble (dissolved) in the composition.

In certain embodiments, the emulsifier is a glyceride emulsifier. In certain embodiments, the emulsifier comprises optionally polyglycolyzed medium- and/or long-chain mono-, di-, and/or tri-glyceride(s).

In certain embodiments, the solubilizer is a polyoxyl castor oil or a vitamin E polyethylene glycol succinate (TPGS).

In certain embodiments, the polyethylene glycol (PEG) has an average molecular weight of about 200 to about 1000 (e.g., about 500 to about 700, or about 550 to about 650, or about 600).

In certain embodiments, the surfactant is polysorbate (e.g., polysorbate 20).

In certain embodiments, the antioxidant is vitamin E. In certain embodiments, the antioxidant is ascorbyl palmitate. In certain embodiments, the antioxidant is butylated hydroxytoluene. In certain embodiments, the antioxidant is triethyl citrate. In certain embodiments, the antioxidant is citric acid.

In certain embodiments, the composition further comprises a co-solvent (e.g., Transcutol®).

Provided herein, in another aspect, is an oral dosage form comprising a pharmaceutical composition, the pharmaceutical composition comprising:

a. at least 40 mg (e.g., at least 50 mg, at least 60 mg, or at least 75 mg) of a compound of Formula (I):

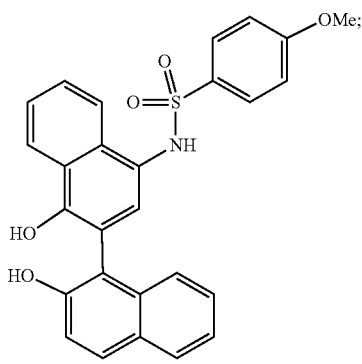

b. an emulsifier (e.g., glyceride), the emulsifier being present in the composition in a weight ratio of compound of Formula (I) to emulsifier of about 1:1 to about 1:2 (e.g., about 1:1.5);
c. a solubilizer, the solubilizer being present in the composition in a weight ratio of compound of Formula (I) to solubilizer of about 1:1 to about 1:5 (e.g., about 1:2 to about 1:4, e.g., about 1:3);
d. a polyethylene glycol (PEG), the polyethylene glycol being present in the composition in a weight ratio of compound of Formula (I) to polyethylene glycol of about 1:2 to about 1:6 (e.g., about 1:3 to about 1:5, e.g., about 1:4);
e. a surfactant, the surfactant being present in the composition in a weight ratio of compound of Formula (I) to surfactant of about 2:1 to about 1:2 (e.g., about 1:1 to about 1:2, e.g. about 1:2); and
f. an (e.g., optional) antioxidant, the antioxidant being present in the composition in a weight ratio of compound of Formula (I) to antioxidant of about 10:1 to about 30:1 (e.g., about 15:1 to about 25:1, e.g., about 20:1).

Provided herein, in another aspect, is an oral dosage form comprising a pharmaceutical composition, the pharmaceutical composition comprising:

a. at least 40 mg (e.g., at least 50 mg, at least 60 mg, or at least 75 mg) of a compound of Formula (I):

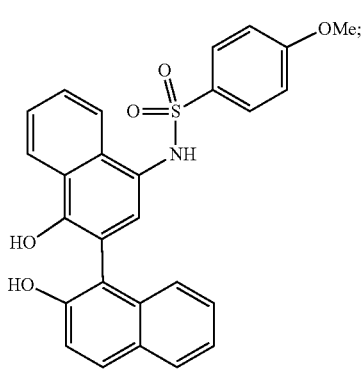

b. an emulsifier (e.g., glyceride), the emulsifier being present in the composition in a weight ratio of compound of Formula (I) to emulsifier of about 1:3 to about 1:7;
c. a solubilizer, the solubilizer being present in the composition in a weight ratio of compound of Formula (I) to solubilizer of about 1:10 to about 1:20 (e.g., about 1:11 to about 1:16);
d. a polyethylene glycol (PEG), the polyethylene glycol being present in the composition in a weight ratio of compound of Formula (I) to polyethylene glycol of about 1:12 to about 1:20 (e.g., about 1:15 to about 1:17);
e. a surfactant, the surfactant being present in the composition in a weight ratio of compound of Formula (I) to surfactant of about 1:2 to about 1:6 (e.g., about 1:3 to about 1:5);
f. an (e.g., optional) antioxidant, the antioxidant being present in the composition in a weight ratio of compound of Formula (I) to antioxidant of about 2:1 to about 20:1 (e.g., about 5:1).

Provided herein, in another aspect, is an oral dosage form comprising a pharmaceutical composition, the pharmaceutical composition comprising at least 40 mg (e.g., at least 50 mg, at least 60 mg, or at least 75 mg) of a compound of Formula (I):

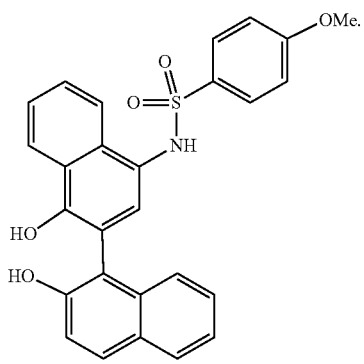

In certain embodiments, the oral dosage form further comprises a capsule. In certain embodiments, the composition is configured entirely within the capsule. In certain embodiments, the capsule is size 00 or smaller.

In certain embodiments, the pharmaceutical composition further comprises an emulsifier (e.g., glyceride). In certain embodiments, the emulsifier is present in the composition in a weight ratio of compound of Formula (I) to the emulsifier of about 1:1 to about 1:2 (e.g., about 1:1.5). In certain embodiments, the emulsifier is present in the composition in a weight ratio of compound of Formula (I) to the emulsifier of about 1:3 to about 1:7.

In certain embodiments, the pharmaceutical composition further comprises a solubilizer. In certain embodiments, the solubilizer is present in the composition in a weight ratio of compound of Formula (I) to solubilizer of about 1:1 to about 1:5 (e.g., about 1:2 to about 1:4, e.g., about 1:3). In certain embodiments, the solubilizer is present in the composition in a weight ratio of compound of Formula (I) to solubilizer of about 1:10 to about 1:20 (e.g., about 1:11 to about 1:16).

In certain embodiments, the pharmaceutical composition further comprises a polyethylene glycol (PEG). In certain embodiments, the polyethylene glycol is present in the composition in a weight ratio of compound of Formula (I) to polyethylene glycol of about 1:2 to about 1:6 (e.g., about 1:3 to about 1:5, e.g., about 1:4). In certain embodiments, the polyethylene glycol is present in the composition in a weight ratio of compound of Formula (I) to polyethylene glycol of about 1:12 to about 1:20 (e.g., about 1:15 to about 1:17).

In certain embodiments, the pharmaceutical composition further comprises a surfactant. In certain embodiments, the surfactant is present in the composition in a weight ratio of compound of Formula (I) to surfactant of about 2:1 to about 1:2 (e.g., about 1:1 to about 1:2, e.g. about 1:2). In certain embodiments, the surfactant is present in the composition in a weight ratio of compound of Formula (I) to surfactant of about 1:2 to about 1:6 (e.g., about 1:3 to about 1:5).

In certain embodiments, the pharmaceutical composition further comprises an antioxidant. In certain embodiments, the antioxidant is present in the composition in a weight ratio of compound of Formula (I) to antioxidant of about 10:1 to about 30:1 (e.g., about 15:1 to about 25:1, e.g., about 20:1). In certain embodiments, the antioxidant is present in the composition in a weight ratio of compound of Formula (I) to antioxidant of about 2:1 to about 20:1 (e.g., about 5:1).

In certain embodiments, the composition is as described in any of the previously described embodiments.

Provided herein, in another aspect, is a method of treating fibrosis, cancer, or chronic inflammation in an individual in need thereof, the method comprising administering to the individual a high dose of a compound of Formula (I):

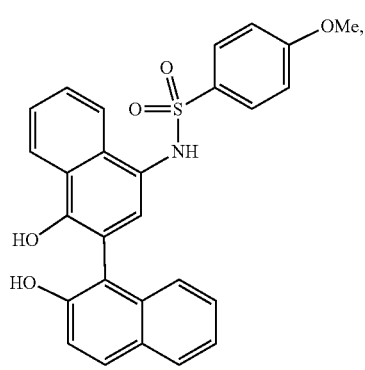

(I)

the high dose of the compound of Formula (I) comprising administration of at least 15 mg/kg/day of the compound of Formula (I) to the individual.

In certain embodiments, administering the compound of Formula (I) comprises administering any pharmaceutical composition, formulation, or oral dosage form described herein. In certain embodiments, the method comprises administering the compound of Formula (I) in any suitable dose. In certain embodiments, the method comprises administering the compound of Formula (I) in any suitable number of oral dosage forms per day. In certain embodiments, the method comprises administering the compound of Formula (I) in a total of no more than 50 oral dosage forms per day. In certain embodiments, the method comprises administering the compound of Formula (I) in a total of no more than 25 oral dosage forms per day. In certain embodiments, the method comprises administering the compound of Formula (I) in a total of no more than 15 oral dosage forms per day.

In certain embodiments, the method comprises administering the compound of Formula (I) in a total of no more than 0.3 oral dosage forms per 1 kg of mass of the individual per day. In certain embodiments, the method comprises administering the compound of Formula (I) in a total of no more than 0.35 oral dosage forms per 1 kg of mass of the individual per day. For example, in an individual weighing 75 kg, the number of oral dosage forms administered per day would not exceed about 26 (i.e., 0.35 oral dosage forms per 1 kg of mass*75 kg of mass=26.25 oral dosage forms).

Provided herein, in another aspect, is a method of treating fibrosis, cancer, or chronic inflammation in an individual in need thereof, the method comprising administering to the individual a plurality of oral dosage forms, the plurality of oral dosage forms collectively comprising a therapeutically effective amount of a compound of Formula (I):

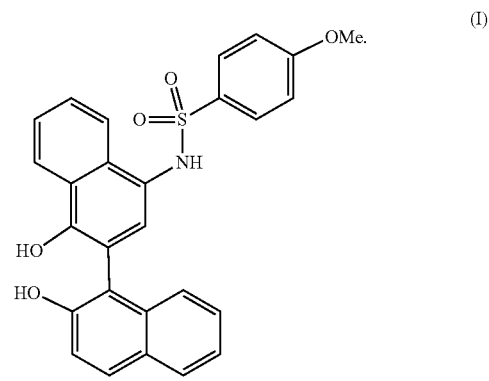 [SMILES: COc1ccc(S(=O)(=O)Nc2cc(-c3c(O)ccc4ccccc34)c(O)c3ccccc23)cc1]

(I)

Provided herein, in another aspect, is a method of treating fibrosis, cancer, or chronic inflammation in an individual in need thereof, the method comprising administering to the individual a plurality of oral dosage forms, the plurality of oral dosage forms collectively comprising a therapeutically effective amount of a compound of Formula (I):

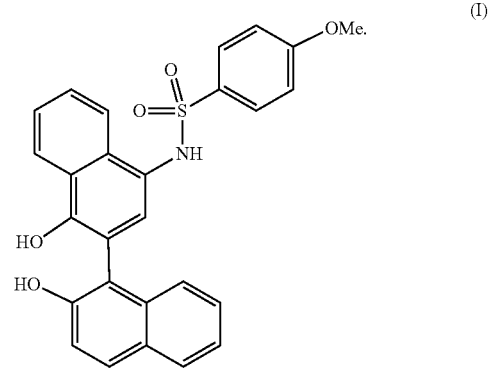 [SMILES: COc1ccc(S(=O)(=O)Nc2cc(-c3c(O)ccc4ccccc34)c(O)c3ccccc23)cc1]

(I)

the plurality of oral dosage forms comprising no more than 0.35 oral dosage forms for every 1 kg of mass of the individual per day (e.g., on average or maximum).

In some embodiments, any suitable (e.g., therapeutically effective) amount of a compound of Formula (I) is provided to an individual, such as an individual in need thereof. In certain embodiments, the amount of compound of Formula (I) varies depending on the disease treated. For example, in some instances, higher doses are utilized in cancer therapies relative to fibrosis or chronic inflammation diseases. In some embodiments, the method comprises administering at least 1 mg/kg/day of the compound of Formula (I) to the individual. In specific embodiments, the method comprises administering at least 2 mg/kg/day of the compound of Formula (I) to the individual. In more specific embodiments, the method comprises administering at least 5 mg/kg/day of the compound of Formula (I) to the individual. In certain embodiments, the method comprises administering at least 10 mg/kg/day of the compound of Formula (I) to the individual. In certain embodiments, the method comprises administering at least 15 mg/kg/day of the compound of Formula (I) to the individual. In certain embodiments, the method comprises administering at least 20 mg/kg/day of the compound of Formula (I) to the individual. In certain embodiments, the method comprises administering at least 25 mg/kg/day of the compound of Formula (I) to the individual. In certain embodiments, the method comprises administering at least 30 mg/kg/day of the compound of Formula (I) to the individual.

In certain embodiments, a cancer treated according to a method provided herein is a liver cancer, lung cancer, head and neck cancer, breast cancer, skin cancer, kidney cancer, testicular cancer, colon cancer, rectal cancer, gastric cancer, metastatic melanoma, prostate cancer, ovarian cancer, cervical cancer, bone cancer, spleen cancer, gall bladder cancer, brain cancer, pancreatic cancer, stomach cancer, anal cancer, prostate cancer, multiple myeloma, post-transplant lymphoproliferative disease, restenosis, myelodysplastic syndrome, leukemia, lymphoma, or acute myelogenous leukemia. In some embodiments, a cancer treated according to a method provided herein is a liver cancer, lung cancer, hepatocellular carcinoma, head and neck squamous cell carcinoma, non-small cell lung cancer, or estrogen receptor-positive breast cancer. In some embodiments, a cancer treated according to a method provided herein is head and neck cancer, lung cancer, liver cancer, breast cancer, ovarian cancer, colon cancer, multiple myeloma, leukemia, or pancreatic cancer. In some embodiments, the leukemia is acute myelogenous leukemia.

In some embodiments, chronic inflammation treated herein is inflammatory bowel disease (IBD), ulcerative colitis, Crohn's disease, asthma, anaphylaxis, cancer cachexia, chronic kidney disease cachexia, nonalcoholic steatohepatitis (NASH), psoriasis, uveitis, scleritis, multiple sclerosis, or pancreatitis. In some embodiments, chronic inflammation treated herein is inflammatory bowel disease (IBD), ulcerative colitis, Crohn's disease, asthma, anaphylaxis, cancer cachexia, chronic kidney disease cachexia, or nonalcoholic steatohepatitis (NASH). In some embodiments, the anaphylaxis comprises anaphylactic shock.

In certain embodiments, the fibrosis is skin fibrosis (or dermal fibrosis), cardiac fibrosis, cirrhosis, pulmonary fibrosis, bone marrow fibrosis, intestine fibrosis, pancreatic fibrosis, joint fibrosis, liver fibrosis, retroperitoneum, renal fibrosis, myelofibrosis, non-alcoholic fatty liver disease, steatohepatitis, systemic sclerosis (including diffuse systemic sclerosis or limited systemic sclerosis), endomyocardial fibrosis, myocardial infarction, atrial fibrosis, mediastinal fibrosis, progressive massive fibrosis, nephrogenic systemic fibrosis, Keloid, arthrofibrosis, adhesive capsulitis, or cystic fibrosis. In certain embodiments, the fibrosis is skin fibrosis (scleroderma), cardiac fibrosis, cirrhosis, pulmonary fibrosis, bone marrow fibrosis, intestine fibrosis, pancreatic fibrosis, joint fibrosis, liver fibrosis, retroperitoneum, myelofibrosis, non-alcoholic fatty liver disease, steatohepatitis, or systemic sclerosis. In certain embodiments, the fibrosis is skin fibrosis (scleroderma), cardiac fibrosis, cirrhosis, or pulmonary fibrosis.

In certain embodiments, the fibrosis is fibrosis following exposure to certain drugs such as chemotherapy, fibrosis following exposure to environmental or other toxins or allergens, fibrosis occurring after an ischemia/reperfusion injury such as myocardial infarction or hypotension, fibrosis occurring after radiation, fibrosis following hepatitis induced by alcohol, toxins, drugs or infections, primary biliary cirrhosis, fibrosis following viral infections involving the heart, liver, or lung, and/or idiopathic retroperitoneal fibrosis.

In certain embodiments, any method provided herein is a method of treating muscle wasting, muscle weakness, or cachexia. The muscle weakness and/or muscle wasting and/or cachexia may have an unknown cause or it may be associated with an underlying condition. The underlying condition may be a catabolic condition. In some embodiments, the underlying medical condition associated with cachexia is least renal failure, cancer, AIDS, HIV infection, chronic obstructive lung disease (including emphysema), multiple sclerosis, congestive heart failure, tuberculosis, familial amyloid polyneuropathy, acrodynia, hormonal deficiency, metabolic acidosis, infectious disease, chronic pancreatitis, autoimmune disorder, celiac disease, Crohn's disease, electrolyte imbalance, Addison's disease, sepsis, burns, trauma, fever, long bone fracture, hyperthyroidism, prolonged steroid therapy, surgery, bone marrow transplant, atypical pneumonia, brucellosis, endocarditis, Hepatitis B, lung abscess, mastocytosis, paraneoplastic syndrome, polyarteritis nodosa, sarcoidosis, systemic lupus erythematosus, myositis, polymyositis, dematomyositis, rheumatological diseases, autoimmune disease, collagen-vascular disease, visceral leishmaniasis, prolonged bed rest, and/or addiction to drugs, such as amphetamine, opiates, or barbitutates.

In certain embodiments, any method provided herein is a method of treating, preventing, or reducing the risk or severity of an allergic reaction. In some embodiments, the allergic reaction is induced following an exposure to an allergen. In some embodiments, the allergen is a food allergen (such as milk, legumes, shellfish, tree nuts, eggs, fish, soy, and wheat), an environmental allergen or seasonal allergen (such as pollen or mold), a venom allergen (such as from wasp, bee, ant, hornet, yellow jacket, or asp), a medication allergen (such as anesthetics, β-lactam antibiotics, aspirin, non-steroidal anti-inflammatory drug, chemotherapy, vaccine, protamine, or herbal preparations), or latex. In some embodiments, the allergic reaction is anaphylaxis, anaphylactic shock, allergic rhinitis, urticaria, food allergy, drug allergy, hymenoptera allerga, bronchial constriction, asthma, or eczema.

In certain embodiments, any method provided herein is a method of treating a viral infection. In some embodiments, the viral infection is a chronic viral infection. In some embodiments, the chronic viral infection is AIDS, HIV infection, Hepatitis B infection, Hepatitis C virus infection, or Epstein-Barr virus infection.

In certain embodiments, any method provided herein is a method of treating graft-versus-host diseases, pulmonary lymphangioleiomyomatosis, chagasic cardiomyopathy, age-related macular degeneration, amyloidosis, astrogliosis in Alzheimer's or other neurodegenerative diseases, or familial amyloid polyneuropathy.

In certain embodiments, any method provided herein is a method of treating a neurodegenerative disease. In some embodiments, the neurodegenerative disease is chemotherapy-induced peripheral neuropathy, diabetic neuropathy, or chemobrain.

In certain embodiments, any method provided herein is a method of treating or reducing the risk or severity of insulin resistance. In some embodiments, the insulin resistance is a result of an underlying condition. In some embodiments, the insulin resistance is associated with muscle of the individual being treated. In some embodiments, the insulin resistance is caused by any reason for the individual, such as elevated free fatty acids in the blood, obesity, being overweight, having visceral fat, having a high fructose intake, having inflammation, being inactive, dysbiosis of the gut microbiota, and/or being genetically predisposed. In certain embodiments, any method provided herein is a method of treating or reducing the risk or severity of medical conditions associated with insulin resistance or that are complications of insulin resistance at least in part, such as severe high blood sugar; severe low blood sugar; heart attack; stroke; kidney disease (including chronic, for example, chronic kidney disease (CKD)); eye problems; cancer; non-alcoholic fatty liver disease (NAFLD); polycystic ovarian syndrome (PCOS); metabolic syndrome; diabetes; or Alzheimer's disease, for example. In certain embodiments, the insulin resistance is a hallmark of metabolic syndrome and type 2 diabetes. Metabolic syndrome is a group of risk factors associated with type 2 diabetes and heart disease. Its symptoms include high blood triglycerides, blood pressure, belly fat, and blood sugar, as well as low HDL (good) cholesterol levels.

In specific embodiments, any method provided herein is a method of treating cancer, such as a cancer described herein. In some other specific embodiments, any method provided herein is a method for treating fibrosis, such as a type of fibrosis or disease or disorder associated therewith described herein. In some other specific embodiments, any method provided herein is a method for treating chronic inflammation, such as any type of chronic inflammation described herein. In certain alternative embodiments, any therapeutic method provided herein is a method of treating a STAT3-mediated disorder, such as by administering a compound of Formula (I) using any administrative method or formulation described herein.

Provided herein, in another aspect, is a method of providing to an individual an improved $C_{max}$ or $AUC_{0-\infty}$ of a compound of Formula (I):

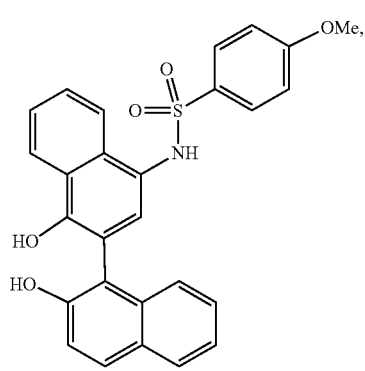

the improved $C_{max}$ or $AUC_{0-\infty}$ being at least 1.1 times (e.g., at least 1.2 times, at least 1.3 times, or more) greater than the effect obtained by administering an otherwise identical amount of a compound of Formula (I) in a formulation of PEG400 and Labrasol® (40:60 by weight).

In certain embodiments, the method has an administration protocol of any of the previously described embodiments. In certain embodiments, the compound of Formula (I) is administered in a pharmaceutical composition or in one or more oral dosage forms of any of the previously described embodiments.

Provided herein, in another aspect, is a crystalline form of a compound of Formula (I).

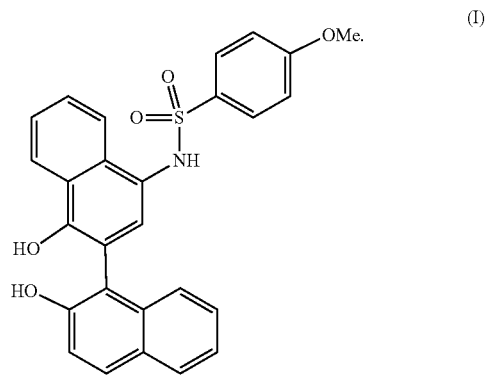 [SMILES: COc1ccc(S(=O)(=O)Nc2cc(-c3c(O)ccc4ccccc34)c(O)c3ccccc23)cc1]

In certain embodiments, the crystalline form is characterized by an X-ray powder diffraction pattern comprising peaks at 8.13±0.2°, 16.50±0.2°, 18.41±0.2°, 21.77±0.2°, and 22.64±0.2° two theta. In certain embodiments, the X-ray powder diffraction pattern further comprises at least one peak selected from 9.56±0.2°, 11.43±0.2°, 12.75±0.2°, and 14.66±0.2° two theta. In certain embodiments, the X-ray powder diffraction pattern further comprises at least one peak selected from 19.70±0.2°, 20.21±0.2°, 20.81±0.2°, and 24.43±0.2° two theta. In certain embodiments, the X-ray powder diffraction pattern further comprises at least one peak selected from 26.10±0.2°, 29.29±0.2°, and 30.75±0.2° two theta. In certain embodiments, the crystalline form is characterized by an X-ray powder diffraction pattern comprising peaks at 8.13±0.2°, 9.56±0.2°, 11.43±0.2°, 12.75±0.2°, 14.66±0.2°, 16.50±0.2°, 18.41±0.2°, from 19.70±0.2°, 20.21±0.2°, 20.81±0.2°, 21.77±0.2°, 22.64±0.2°, 24.43±0.2°, 26.10±0.2°, 29.29±0.2°, and 30.75±0.2° two theta.

In certain embodiments, the crystalline form is characterized by an X-ray powder diffraction pattern substantially as set forth in FIG. 1.

In certain embodiments, any method provided herein comprises administering a compound of Formula (I) having a crystalline form described herein.

BRIEF DESCRIPTION OF THE DRAWINGS

Various features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 4 shows the design of the rat pharmacokinetics study of various formulations of a compound of Formula (I).

FIG. 5 shows the individual human pharmacokinetic parameters by cohort for the 12-hour time course of a single dose of the two-component formulation system.

FIG. 6 shows the mean human pharmacokinetic parameters by cohort for the 12-hour time course of a single dose of the two-component formulation system.

DETAILED DESCRIPTION OF THE INVENTION

Figure 1:
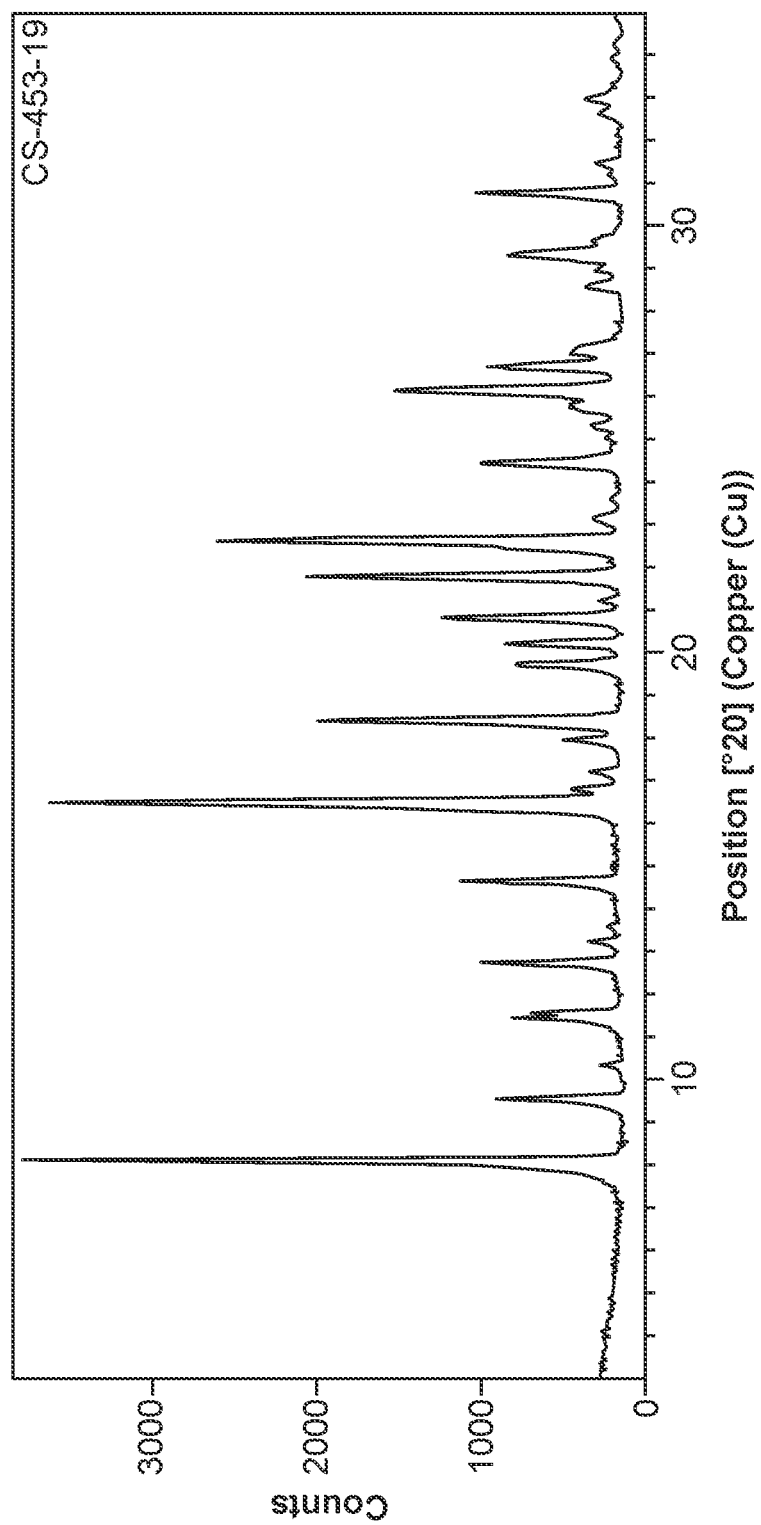
FIG. 1 shows the X-ray powder diffraction (XRPD) pattern of the crystalline form of the compound of Formula (I).

The term "oral dosage form" as used herein and unless otherwise indicated, refers to a pharmaceutical composition that has been formulated or otherwise prepared for oral administration, such as in a discrete form.

Provided in certain embodiments herein are compositions, formulations, and oral dosage forms comprising a compound of Formula (I):

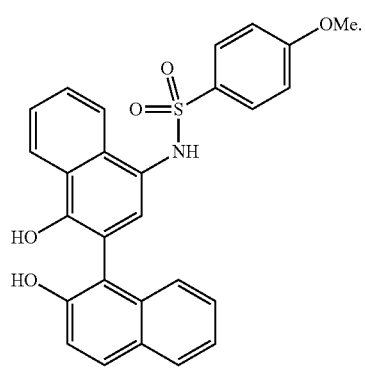

(I)

In some embodiments, the compositions, formulations, and oral dosage forms described herein comprise a compound of Formula (I) as a pharmaceutically acceptable salt, a hydrate, or a solvate.

Also provided herein are methods of using a compound of Formula (I), such as in therapeutic or other methods described herein. In some embodiments, the methods involve the use of (e.g., comprise the administration of) a compound of Formula (I), wherein the compound of Formula (I) is formulated in a manner described herein (e.g., is present in a composition as described herein). In some embodiments, a compound of Formula (I) (e.g., as formulated herein) is utilized in a method for treating a disease or disorder mediated by STAT3, or a disease or disorder that is otherwise treatable with a STAT3 inhibitor. In specific embodiments, provided herein are methods of treating cancer. In other specific embodiments, provided herein are methods of treating fibrosis. In still other specific embodiments, provided herein are methods of treating chronic inflammation.

While a compound of Formula (I) is generally considered to be highly insoluble ("brick dust"), in certain instances, such compositions provided are able to provide high loading of a compound of Formula (I), good ability to solubilize a compound of Formula (I), good ability to provide for high bioavailability of a compound of Formula (I), good stability (e.g., chemical and/or physical stability), and/or reduce pill burden for individuals receiving therapies involving the administration of a compound of Formula (I). Also provided in various embodiments herein are methods, such as therapeutic methods for cancer, fibrosis, and/or chronic inflammation, involving the administration of a compound of Formula (I) or compositions or formulations provided herein.

In some embodiments, a composition, formulation or oral dosage form provided herein comprises, in addition to the compound of Formula (I), any suitable excipient or combination of excipients. In certain embodiments, the excipient or combination of excipients is suitable for providing good solubility of a compound of Formula (I), good physical stability (e.g., good solubility and/or dispersion of a compound of Formula (I)), good chemical stability of a compound of Formula (I), good (e.g., oral) bioavailability of a compound of Formula (I), and/or desirable or therapeutic effect, with a manageable (e.g., fewer than 25 pills per day, or other amount described herein) or reduced pill burden (e.g., relative to two component excipient systems described herein).

In some embodiments, provided herein is a (e.g., pharmaceutical) composition comprising a compound of Formula (I) and an emulsifier, a solubilizer, a solvent, a surfactant, and/or an antioxidant. In specific embodiments, the composition comprises a solvent and a solubilizer. In more specific embodiments, the composition comprises an emulsifier, a solubilizer, and a solvent. In still more specific embodiments, the composition comprises an emulsifier, a solubilizer, a surfactant, and a solvent. In yet more specific embodiments, the composition comprises an emulsifier, a solubilizer, a surfactant, an antioxidant, and a solvent. In certain embodiments, the composition or formulation is a self-emulsifying drug dispersion (SEDD).

In certain embodiments, the composition, dosage form, or formulation described herein has a pill burden at least 2-fold lower than (i.e., ½) that of the 60:40 Labrasol®/PEG400 formulation. In certain embodiments, the composition, dosage form, or formulation described herein has a pill burden at least 2.1-fold lower than that of the 60:40 Labrasol®/PEG400 formulation. In certain embodiments, the formulation described herein has a pill burden at least 2.2-fold lower than that of the 60:40 Labrasol®/PEG400 formulation. In certain embodiments, the composition, dosage form, or formulation described herein has a pill burden at least 2.3-fold lower than that of the 60:40 Labrasol®/PEG400 formulation. In certain embodiments, the composition, dosage form, or formulation described herein has a pill burden at least 2.4-fold lower than that of the 60:40 Labrasol®/PEG400 formulation. In certain embodiments, the composition, dosage form, or formulation described herein has a pill burden at least 2.5-fold lower than that of the 60:40 Labrasol®/PEG400 formulation. In certain embodiments, the composition, dosage form, or formulation described herein has a pill burden at least 2.6-fold lower than that of the 60:40 Labrasol®/PEG400 formulation. In certain embodiments, the composition, dosage form, or formulation described herein has a pill burden at least 2.7-fold lower than that of the 60:40 Labrasol®/PEG400 formulation.

In certain embodiments, the composition, dosage form, or formulation described herein displays a droplet size of no more than 200 nm when dispersed in (e.g., simulated) gastric/intestinal fluids. In certain embodiments, the composition, dosage form, or formulation described herein displays a droplet size of no more than 175 nm when dispersed in (e.g., simulated) gastric/intestinal fluids. In certain embodiments, the composition, dosage form, or formulation described herein displays a droplet size of no more than 150 nm when dispersed in (e.g., simulated) gastric/intestinal fluids. In certain embodiments, the composition, dosage form, or formulation described herein displays a droplet size of no more than 125 nm when dispersed in (e.g., simulated) gastric/intestinal fluids.

In certain embodiments, the composition, dosage form, or formulation described herein displays a polydispersity index of no more than 0.5 when dispersed in (e.g., simulated) gastric/intestinal fluids. In certain embodiments, the composition, dosage form, or formulation described herein displays a polydispersity index of no more than 0.45 when dispersed in (e.g., simulated) gastric/intestinal fluids. In certain embodiments, the composition, dosage form, or formulation described herein displays a polydispersity index of no more than 0.4 when dispersed in (e.g., simulated) gastric/intestinal fluids. In certain embodiments, the composition, dosage form, or formulation described herein displays a polydispersity index of no more than 0.35 when dispersed in (e.g., simulated) gastric/intestinal fluids. In certain embodiments, the composition, dosage form, or formulation described herein displays a polydispersity index of no more than 0.3 when dispersed in (e.g., simulated) gastric/intestinal fluids. In certain embodiments, the composition, dosage form, or formulation described herein displays a polydispersity index of no more than 0.25 when dispersed in (e.g., simulated) gastric/intestinal fluids.

In certain embodiments, the composition, dosage form, or formulation described herein possesses a compound of Formula (I) purity of at least 85% after 5 months (e.g., at room temperature and 60% RH). In certain embodiments, the composition, dosage form, or formulation described herein possesses a compound of Formula (I) purity of at least 90% after 5 months (e.g., at room temperature and 60% RH). In certain embodiments, the composition, dosage form, or formulation described herein possesses a compound of Formula (I) purity of at least 95% after 5 months (e.g., at room temperature and 60% RH). In certain embodiments, the composition, dosage form, or formulation described herein possesses a compound of Formula (I) purity of at least 96% after 5 months (e.g., at room temperature and 60% RH). In certain embodiments, the composition, dosage form, or formulation described herein possesses a compound of Formula (I) purity of at least 97% after 5 months (e.g., at room temperature and 60% RH). In certain embodiments, the composition, dosage form, or formulation described herein possesses a compound of Formula (I) purity of at least 98% after 5 months (e.g., at room temperature and 60% RH).

In certain embodiments, the composition, dosage form, or formulation described herein possesses a greater (e.g., at least 1.05 times, at least 1.1 times, at least 1.15 times, at least 1.2 times, at least 1.25 times, at least 1.3 times, or more) $C_{max}$ than an otherwise similarly provided 60:40 Labrasol®/PEG400 formulation of a compound of Formula (I). In certain embodiments, the composition, dosage form, or formulation described herein possesses a comparable (e.g., about 80-120%, about 90-110%, or the like) total systemic exposure ($AUC_{last}$) and dose-normalized AUC ($AUC_\infty\_D\_obs$) to an otherwise similarly provided 60:40 Labrasol®/PEG400 formulation of a compound of Formula (I).

Provided herein, in one aspect, is a pharmaceutical composition comprising:
a. a therapeutically effective amount of a compound of Formula (I):

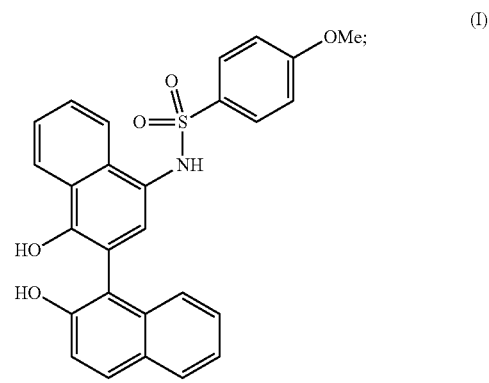 [SMILES: COc1ccc(S(=O)(=O)Nc2cc(-c3c(O)ccc4ccccc34)c(O)c3ccccc23)cc1]

b. an emulsifier (e.g., glyceride), the emulsifier being present in the composition in a weight ratio of compound of Formula (I) to the emulsifier of about 1:1 to about 1:2 (e.g., about 1:1.5);
c. a solubilizer, the solubilizer being present in the composition in a weight ratio of compound of Formula (I) to solubilizer of about 1:1 to about 1:5 (e.g., about 1:2 to about 1:4, e.g., about 1:3);
d. a polyethylene glycol (PEG), the polyethylene glycol being present in the composition in a weight ratio of compound of Formula (I) to polyethylene glycol of about 1:2 to about 1:6 (e.g., about 1:3 to about 1:5, e.g., about 1:4);
e. a surfactant, the surfactant being present in the composition in a weight ratio of compound of Formula (I) to surfactant of about 2:1 to about 1:2 (e.g., about 1:1 to about 1:2, e.g. about 1:2); and
f. an antioxidant, the antioxidant being present in the composition in a weight ratio of compound of Formula (I) to antioxidant of about 10:1 to about 30:1 (e.g., about 15:1 to about 25:1, e.g., about 20:1).

Provided herein, in one aspect, is a pharmaceutical composition comprising:
a. a therapeutically effective amount of a compound of Formula (I):

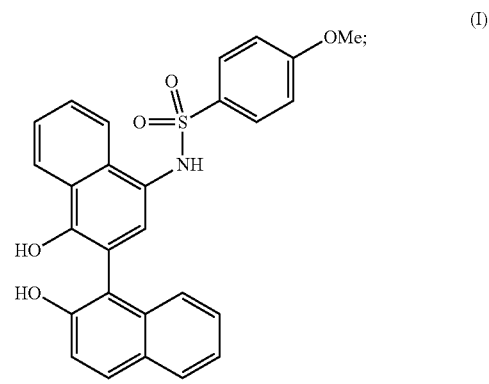 [SMILES: COc1ccc(S(=O)(=O)Nc2cc(-c3c(O)ccc4ccccc34)c(O)c3ccccc23)cc1]

b. an emulsifier (e.g., glyceride), the emulsifier being present in the composition in a weight ratio of compound of Formula (I) to the emulsifier of about 1:3 to about 1:7;

c. a solubilizer, the solubilizer being present in the composition in a weight ratio of compound of Formula (I) to solubilizer of about 1:10 to about 1:20 (e.g., about 1:11 to about 1:16);
d. a polyethylene glycol (PEG), the polyethylene glycol being present in the composition in a weight ratio of compound of Formula (I) to polyethylene glycol of about 1:12 to about 1:20 (e.g., about 1:15 to about 1:17);
e. a surfactant, the surfactant being present in the composition in a weight ratio of compound of Formula (I) to surfactant of about 1:2 to about 1:6 (e.g., about 1:3 to about 1:5);
f. an antioxidant, the antioxidant being present in the composition in a weight ratio of compound of Formula (I) to antioxidant of about 2:1 to about 20:1 (e.g., about 5:1).

In certain embodiments, the emulsifier is present in the composition in a weight ratio of compound of Formula (I) to the emulsifier of about 1:1. In certain embodiments, the emulsifier is present in the composition in a weight ratio of compound of Formula (I) to the emulsifier of about 1:2. In certain embodiments, the emulsifier is present in the composition in a weight ratio of compound of Formula (I) to the emulsifier of about 1:3. In certain embodiments, the emulsifier is present in the composition in a weight ratio of compound of Formula (I) to the emulsifier of about 1:4. In certain embodiments, the emulsifier is present in the composition in a weight ratio of compound of Formula (I) to the emulsifier of about 1:5. In certain embodiments, the emulsifier is present in the composition in a weight ratio of compound of Formula (I) to the emulsifier of about 1:6. In certain embodiments, the emulsifier is present in the composition in a weight ratio of compound of Formula (I) to the emulsifier of about 1:7. In certain embodiments, the emulsifier is present in the composition in a weight ratio of compound of Formula (I) to the emulsifier of about 1:1.5.

In certain embodiments, the solubilizer is present in the composition in a weight ratio of compound of Formula (I) to solubilizer of about 1:1. In certain embodiments, the solubilizer is present in the composition in a weight ratio of compound of Formula (I) to solubilizer of about 1:2. In certain embodiments, the solubilizer is present in the composition in a weight ratio of compound of Formula (I) to solubilizer of about 1:3. In certain embodiments, the solubilizer is present in the composition in a weight ratio of compound of Formula (I) to solubilizer of about 1:4. In certain embodiments, the solubilizer is present in the composition in a weight ratio of compound of Formula (I) to solubilizer of about 1:5. In certain embodiments, the solubilizer is present in the composition in a weight ratio of compound of Formula (I) to solubilizer of about 1:4. In certain embodiments, the solubilizer is present in the composition in a weight ratio of compound of Formula (I) to solubilizer of about 1:6. In certain embodiments, the solubilizer is present in the composition in a weight ratio of compound of Formula (I) to solubilizer of about 1:4. In certain embodiments, the solubilizer is present in the composition in a weight ratio of compound of Formula (I) to solubilizer of about 1:7. In certain embodiments, the solubilizer is present in the composition in a weight ratio of compound of Formula (I) to solubilizer of about 1:4. In certain embodiments, the solubilizer is present in the composition in a weight ratio of compound of Formula (I) to solubilizer of about 1:8. In certain embodiments, the solubilizer is present in the composition in a weight ratio of compound of Formula (I) to solubilizer of about 1:4. In certain embodiments, the solubilizer is present in the composition in a weight ratio of compound of Formula (I) to solubilizer of about 1:9. In certain embodiments, the solubilizer is present in the composition in a weight ratio of compound of Formula (I) to solubilizer of about 1:10. In certain embodiments, the solubilizer is present in the composition in a weight ratio of compound of Formula (I) to solubilizer of about 1:11. In certain embodiments, the solubilizer is present in the composition in a weight ratio of compound of Formula (I) to solubilizer of about 1:12. In certain embodiments, the solubilizer is present in the composition in a weight ratio of compound of Formula (I) to solubilizer of about 1:13. In certain embodiments, the solubilizer is present in the composition in a weight ratio of compound of Formula (I) to solubilizer of about 1:14. In certain embodiments, the solubilizer is present in the composition in a weight ratio of compound of Formula (I) to solubilizer of about 1:15. In certain embodiments, the solubilizer is present in the composition in a weight ratio of compound of Formula (I) to solubilizer of about 1:16. In certain embodiments, the solubilizer is present in the composition in a weight ratio of compound of Formula (I) to solubilizer of about 1:17. In certain embodiments, the solubilizer is present in the composition in a weight ratio of compound of Formula (I) to solubilizer of about 1:18. In certain embodiments, the solubilizer is present in the composition in a weight ratio of compound of Formula (I) to solubilizer of about 1:19. In certain embodiments, the solubilizer is present in the composition in a weight ratio of compound of Formula (I) to solubilizer of about 1:20.

In certain embodiments, the polyethylene glycol is present in the composition in a weight ratio of compound of Formula (I) to polyethylene glycol of about 1:1. In certain embodiments, the polyethylene glycol is present in the composition in a weight ratio of compound of Formula (I) to polyethylene glycol of about 1:2. In certain embodiments, the polyethylene glycol is present in the composition in a weight ratio of compound of Formula (I) to polyethylene glycol of about 1:3. In certain embodiments, the polyethylene glycol is present in the composition in a weight ratio of compound of Formula (I) to polyethylene glycol of about 1:4. In certain embodiments, the polyethylene glycol is present in the composition in a weight ratio of compound of Formula (I) to polyethylene glycol of about 1:5. In certain embodiments, the polyethylene glycol is present in the composition in a weight ratio of compound of Formula (I) to polyethylene glycol of about 1:6. In certain embodiments, the polyethylene glycol is present in the composition in a weight ratio of compound of Formula (I) to polyethylene glycol of about 1:7. In certain embodiments, the polyethylene glycol is present in the composition in a weight ratio of compound of Formula (I) to polyethylene glycol of about 1:8. In certain embodiments, the polyethylene glycol is present in the composition in a weight ratio of compound of Formula (I) to polyethylene glycol of about 1:9. In certain embodiments, the polyethylene glycol is present in the composition in a weight ratio of compound of Formula (I) to polyethylene glycol of about 1:10. In certain embodiments, the polyethylene glycol is present in the composition in a weight ratio of compound of Formula (I) to polyethylene glycol of about 1:11. In certain embodiments, the polyethylene glycol is present in the composition in a weight ratio of compound of Formula (I) to polyethylene glycol of about 1:12. In certain embodiments, the polyethylene glycol is present in the composition in a weight ratio of compound of Formula (I) to polyethylene glycol of about 1:13. In certain embodiments, the polyethylene glycol is present in the composition in a weight ratio of compound of Formula (I) to polyethylene glycol of about 1:14. In certain embodiments, the polyethylene glycol is present in the composition in a weight ratio of compound of Formula (I) to polyethylene glycol of about 1:15. In certain embodiments, the polyethylene glycol is present in the composition in a weight ratio of compound of Formula (I) to polyethylene glycol of about 1:16. In certain embodiments, the polyethylene glycol is present in the composition in a weight ratio of compound of Formula (I) to polyethylene glycol of about 1:17. In certain embodiments, the polyethylene glycol is present in the composition in a weight ratio of compound of Formula (I) to polyethylene glycol of about 1:18. In certain embodiments, the polyethylene glycol is present in the composition in a weight ratio of compound of Formula (I) to polyethylene glycol of about 1:19. In certain embodiments, the polyethylene glycol is present in the composition in a weight ratio of compound of Formula (I) to polyethylene glycol of about 1:20.

In certain embodiments, the surfactant is present in the composition in a weight ratio of compound of Formula (I) to surfactant of about 4:1. In certain embodiments, the surfactant is present in the composition in a weight ratio of compound of Formula (I) to surfactant of about 3:1. In certain embodiments, the surfactant is present in the composition in a weight ratio of compound of Formula (I) to surfactant of about 2:1. In certain embodiments, the surfactant is present in the composition in a weight ratio of compound of Formula (I) to surfactant of about 1:1. In certain embodiments, the surfactant is present in the composition in a weight ratio of compound of Formula (I) to surfactant of about 1:2. In certain embodiments, the surfactant is present in the composition in a weight ratio of compound of Formula (I) to surfactant of about 1:3. In certain embodiments, the surfactant is present in the composition in a weight ratio of compound of Formula (I) to surfactant of about 1:4. In certain embodiments, the surfactant is present in the composition in a weight ratio of compound of Formula (I) to surfactant of about 1:5. In certain embodiments, the surfactant is present in the composition in a weight ratio of compound of Formula (I) to surfactant of about 1:6.

In certain embodiments, the antioxidant is present in the composition in a weight ratio of compound of Formula (I) to antioxidant of about 2:1. In certain embodiments, the antioxidant is present in the composition in a weight ratio of compound of Formula (I) to antioxidant of about 3:1. In certain embodiments, the antioxidant is present in the composition in a weight ratio of compound of Formula (I) to antioxidant of about 4:1. In certain embodiments, the antioxidant is present in the composition in a weight ratio of compound of Formula (I) to antioxidant of about 5:1. In certain embodiments, the antioxidant is present in the composition in a weight ratio of compound of Formula (I) to antioxidant of about 6:1. In certain embodiments, the antioxidant is present in the composition in a weight ratio of compound of Formula (I) to antioxidant of about 7:1. In certain embodiments, the antioxidant is present in the composition in a weight ratio of compound of Formula (I) to antioxidant of about 8:1. In certain embodiments, the antioxidant is present in the composition in a weight ratio of compound of Formula (I) to antioxidant of about 9:1. In certain embodiments, the antioxidant is present in the composition in a weight ratio of compound of Formula (I) to antioxidant of about 10:1. In certain embodiments, the antioxidant is present in the composition in a weight ratio of compound of Formula (I) to antioxidant of about 11:1. In certain embodiments, the antioxidant is present in the composition in a weight ratio of compound of Formula (I) to antioxidant of about 12:1. In certain embodiments, the antioxidant is present in the composition in a weight ratio of compound of Formula (I) to antioxidant of about 13:1. In certain embodiments, the antioxidant is present in the composition in a weight ratio of compound of Formula (I) to antioxidant of about 14:1. In certain embodiments, the antioxidant is present in the composition in a weight ratio of compound of Formula (I) to antioxidant of about 15:1. In certain embodiments, the antioxidant is present in the composition in a weight ratio of compound of Formula (I) to antioxidant of about 16:1. In certain embodiments, the antioxidant is present in the composition in a weight ratio of compound of Formula (I) to antioxidant of about 17:1. In certain embodiments, the antioxidant is present in the composition in a weight ratio of compound of Formula (I) to antioxidant of about 18:1. In certain embodiments, the antioxidant is present in the composition in a weight ratio of compound of Formula (I) to antioxidant of about 19:1. In certain embodiments, the antioxidant is present in the composition in a weight ratio of compound of Formula (I) to antioxidant of about 20:1. In certain embodiments, the antioxidant is present in the composition in a weight ratio of compound of Formula (I) to antioxidant of about 21:1. In certain embodiments, the antioxidant is present in the composition in a weight ratio of compound of Formula (I) to antioxidant of about 22:1. In certain embodiments, the antioxidant is present in the composition in a weight ratio of compound of Formula (I) to antioxidant of about 23:1. In certain embodiments, the antioxidant is present in the composition in a weight ratio of compound of Formula (I) to antioxidant of about 24:1. In certain embodiments, the antioxidant is present in the composition in a weight ratio of compound of Formula (I) to antioxidant of about 25:1. In certain embodiments, the antioxidant is present in the composition in a weight ratio of compound of Formula (I) to antioxidant of about 26:1. In certain embodiments, the antioxidant is present in the composition in a weight ratio of compound of Formula (I) to antioxidant of about 27:1. In certain embodiments, the antioxidant is present in the composition in a weight ratio of compound of Formula (I) to antioxidant of about 28:1. In certain embodiments, the antioxidant is present in the composition in a weight ratio of compound of Formula (I) to antioxidant of about 29:1. In certain embodiments, the antioxidant is present in the composition in a weight ratio of compound of Formula (I) to antioxidant of about 30:1.

In certain embodiments, the composition is or is a part of a self-emulsifying drug dispersion (SEDD). In certain embodiments, the composition is a capsule fill formulation. In certain embodiments, the composition further comprises a capsule shell.

In certain embodiments, the compound of Formula (I) is present in the formulation in a concentration of at least 50 mg/g (e.g., at least 60 mg/g, at least 70 mg/g, at least 80 mg/g, or at least 90 mg/g) (e.g., excluding the mass of a capsule shell). In certain embodiments, the compound of Formula (I) is present in the formulation in a concentration of at least 50 mg/g. In certain embodiments, the compound of Formula (I) is present in the formulation in a concentration of at least 60 mg/g. In certain embodiments, the compound of Formula (I) is present in the formulation in a concentration of at least 70 mg/g. In certain embodiments, the compound of Formula (I) is present in the formulation in a concentration of at least 80 mg/g. In certain embodiments, the compound of Formula (I) is present in the formulation in a concentration of at least 90 mg/g.

In certain embodiments, the compound of Formula (I) is present in the formulation in a concentration of at least 60 mg/mL (e.g., at least 70 mg/mL, at least 80 mg/mL, at least 90 mg/mL, or at least 100 mg/mL) (e.g., excluding the volume of a capsule shell). In certain embodiments, the compound of Formula (I) is present in the formulation in a concentration of at least 60 mg/mL. In certain embodiments, the compound of Formula (I) is present in the formulation in a concentration of at least 70 mg/mL. In certain embodiments, the compound of Formula (I) is present in the formulation in a concentration of at least 80 mg/mL. In certain embodiments, the compound of Formula (I) is present in the formulation in a concentration of at least 90 mg/mL. In certain embodiments, the compound of Formula (I) is present in the formulation in a concentration of at least 100 mg/mL.

In certain embodiments, at least 60 wt. % (e.g., at least 80 wt. %, at least 90 wt. %, or at least 95 wt. %) of the compound of Formula (I) is soluble (dissolved) in the composition. In certain embodiments, at least 60 wt. % of the compound of Formula (I) is soluble (dissolved) in the composition. In certain embodiments, at least 80 wt. % of the compound of Formula (I) is soluble (dissolved) in the composition. In certain embodiments, at least 90 wt. % of the compound of Formula (I) is soluble (dissolved) in the composition. In certain embodiments, at least 95 wt. % of the compound of Formula (I) is soluble (dissolved) in the composition.

In certain embodiments, the emulsifier is a glyceride emulsifier. In certain embodiments, the emulsifier comprises optionally polyglycolyzed medium- and/or long-chain mono-, di-, and/or tri-glyceride(s). In certain embodiments, the emulsifier comprises a medium-chain mono-glyceride. In certain embodiments, the emulsifier comprises a polyglycolyzed medium-chain mono-glyceride. In certain embodiments, the emulsifier comprises a long-chain mono-glyceride. In certain embodiments, the emulsifier comprises a polyglycolyzed long-chain mono-glyceride. In certain embodiments, the emulsifier comprises a medium-chain di-glyceride. In certain embodiments, the emulsifier comprises a polyglycolyzed medium-chain di-glyceride. In certain embodiments, the emulsifier comprises a long-chain di-glyceride. In certain embodiments, the emulsifier comprises a polyglycolyzed long-chain di-glyceride. In certain embodiments, the emulsifier comprises a medium-chain tri-glyceride. In certain embodiments, the emulsifier comprises a polyglycolyzed medium-chain tri-glyceride. In certain embodiments, the emulsifier comprises a long-chain tri-glyceride. In certain embodiments, the emulsifier comprises a polyglycolyzed long-chain tri-glyceride.

In certain embodiments, the emulsifier is Labrasol®. In certain embodiments, the emulsifier is Capmul® MCM. In certain embodiments, the emulsifier is Capmul® MCM EP. In certain embodiments, the emulsifier is Capmul® C8 EP. In certain embodiments, the emulsifier is Capryol® 90.

In certain embodiments, the solubilizer is a polyoxyl castor oil or a vitamin E polyethylene glycol succinate (TPGS). In certain embodiments, the solubilizer is a polyoxyl castor oil. In certain embodiments, the solubilizer is a vitamin E polyethylene glycol succinate. In certain embodiments, the surfactant is Kolliphor® RH 40. In certain embodiments, the solubilizer is Vitamin E TPGS.

In certain embodiments, the polyethylene glycol (PEG) has an average molecular weight of about 200 to about 1000 (e.g., about 500 to about 700, or about 550 to about 650, or about 600). In certain embodiments, the polyethylene glycol (PEG) has an average molecular weight of about 200 to 1000. In certain embodiments, the polyethylene glycol (PEG) has an average molecular weight of about 500 to 700. In certain embodiments, the polyethylene glycol (PEG) has an average molecular weight of about 550 to 650. In certain embodiments, the polyethylene glycol (PEG) has an average molecular weight of about 600.

In certain embodiments, the polyethylene glycol (PEG) is PEG200. In certain embodiments, the polyethylene glycol (PEG) is PEG300. In certain embodiments, the polyethylene glycol (PEG) is PEG400. In certain embodiments, the polyethylene glycol (PEG) is PEG500. In certain embodiments, the polyethylene glycol (PEG) is PEG600. In certain embodiments, the polyethylene glycol (PEG) is PEG700. In certain embodiments, the polyethylene glycol (PEG) is PEG800. In certain embodiments, the polyethylene glycol (PEG) is PEG900. In certain embodiments, the polyethylene glycol (PEG) is PEG1000.

In certain embodiments, the surfactant is polysorbate (e.g., polysorbate 20). In certain embodiments, the surfactant is polysorbate 20. In certain embodiments, the surfactant is polysorbate 40. In certain embodiments, the surfactant is polysorbate 60. In certain embodiments, the surfactant is polysorbate 80.

In certain embodiments, the antioxidant is vitamin E. In certain embodiments, the antioxidant is ascorbyl palmitate. In certain embodiments, the antioxidant is butylated hydroxytoluene. In certain embodiments, the antioxidant is triethyl citrate. In certain embodiments, the antioxidant is citric acid.

In certain embodiments, the composition further comprises a co-solvent (e.g., Transcutol®). In certain embodiments, the composition further comprises Transcutol® HP.

Provided herein, in another aspect, is an oral dosage form comprising a pharmaceutical composition, the pharmaceutical composition comprising:
a. at least 40 mg (e.g., at least 50 mg, at least 60 mg, at least 75 mg) of a compound of Formula (I):

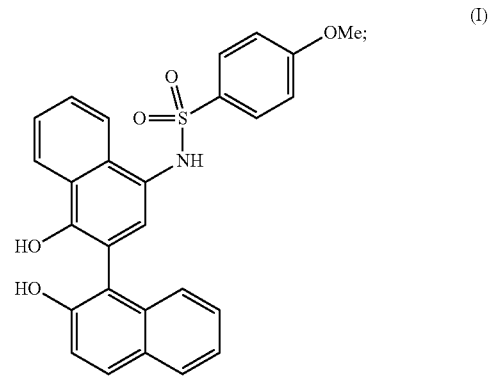 [SMILES: COc1ccc(S(=O)(=O)Nc2cc(-c3c(O)ccc4ccccc34)c(O)c3ccccc23)cc1]

b. an emulsifier (e.g., glyceride), the emulsifier being present in the composition in a weight ratio of compound of Formula (I) to emulsifier of about 1:1 to about 1:2 (e.g., about 1:1.5);
c. a solubilizer, the solubilizer being present in the composition in a weight ratio of compound of Formula (I) to solubilizer of about 1:1 to about 1:5 (e.g., about 1:2 to about 1:4, e.g., about 1:3);
d. a polyethylene glycol (PEG), the polyethylene glycol being present in the composition in a weight ratio of compound of Formula (I) to polyethylene glycol of about 1:2 to about 1:6 (e.g., about 1:3 to about 1:5, e.g., about 1:4);

e. a surfactant, the surfactant being present in the composition in a weight ratio of compound of Formula (I) to surfactant of about 2:1 to about 1:2 (e.g., about 1:1 to about 1:2, e.g. about 1:2); and f. an antioxidant, the antioxidant being present in the composition in a weight ratio of compound of Formula (I) to antioxidant of about 10:1 to about 30:1 (e.g., about 15:1 to about 25:1, e.g., about 20:1).

Provided herein, in another aspect, is an oral dosage form comprising a pharmaceutical composition, the pharmaceutical composition comprising:

a. at least 40 mg (e.g., at least 50 mg, at least 60 mg, at least 75 mg) of a compound of Formula (I):

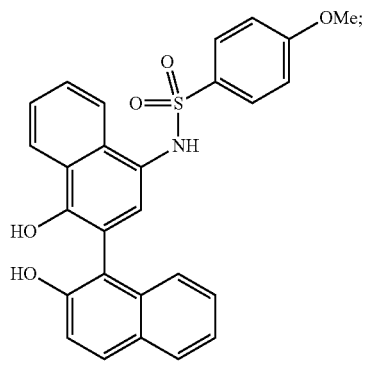

b. an emulsifier (e.g., glyceride), the emulsifier being present in the composition in a weight ratio of compound of Formula (I) to emulsifier of about 1:3 to about 1:7;

c. a solubilizer, the solubilizer being present in the composition in a weight ratio of compound of Formula (I) to solubilizer of about 1:10 to about 1:20 (e.g., about 1:11 to about 1:16);

d. a polyethylene glycol (PEG), the polyethylene glycol being present in the composition in a weight ratio of compound of Formula (I) to polyethylene glycol of about 1:12 to about 1:20 (e.g., about 1:15 to about 1:17);

e. a surfactant, the surfactant being present in the composition in a weight ratio of compound of Formula (I) to surfactant of about 1:2 to about 1:6 (e.g., about 1:3 to about 1:5);

f. an antioxidant, the antioxidant being present in the composition in a weight ratio of compound of Formula (I) to antioxidant of about 2:1 to about 20:1 (e.g., about 5:1).

Provided herein, in another aspect, is an oral dosage form comprising a pharmaceutical composition, the pharmaceutical composition comprising at least 40 mg (e.g., at least 50 mg, at least 60 mg, or at least 75 mg) of a compound of Formula (I):

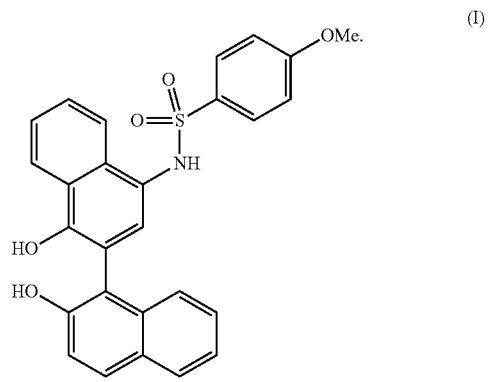 [SMILES: COc1ccc(S(=O)(=O)Nc2cc(-c3c(O)ccc4ccccc34)c(O)c3ccccc23)cc1]

In certain embodiments, the pharmaceutical composition comprises at least 40 mg of a compound of Formula (I). In certain embodiments, the pharmaceutical composition comprises at least 50 mg of a compound of Formula (I). In certain embodiments, the pharmaceutical composition comprises at least 60 mg of a compound of Formula (I). In certain embodiments, the pharmaceutical composition comprises at least 75 mg of a compound of Formula (I).

In certain embodiments, the oral dosage form further comprises a capsule. In certain embodiments, the composition is configured entirely within the capsule.

In certain embodiments, the capsule is size 00 or smaller. In certain embodiments, the capsule is size 00. In certain embodiments, the capsule is size 0E. In certain embodiments, the capsule is size 0. In certain embodiments, the capsule is size 1. In certain embodiments, the capsule is size 2. In certain embodiments, the capsule is size 3. In certain embodiments, the capsule is size 4. In certain embodiments, the capsule is size 5.

In certain embodiments, the capsule is size 00E or larger. In certain embodiments, the capsule is size OOE. In certain embodiments, the capsule is size 000.

A size 5 capsule possesses a volume of 0.13 mL. A size 4 capsule possesses a volume of 0.20 mL. A size 3 capsule possesses a volume of 0.27 mL. A size 2 capsule possesses a volume of 0.36 mL. A size 1 capsule possesses a volume of 0.48 mL. A size 0 capsule possesses a volume of 0.68 mL. A size OE capsule possesses a volume of 0.78 mL. A size 00 capsule possesses a volume of 0.90 mL. A size OOE capsule possesses a volume of 1.00 mL. A size 000 capsule possesses a volume of 1.37 mL.

In certain embodiments, the pharmaceutical composition further comprises an emulsifier (e.g., glyceride).

In certain embodiments, the emulsifier is present in the composition in a weight ratio of compound of Formula (I) to the emulsifier of about 1:1 to about 1:2 (e.g., about 1:1.5). In certain embodiments, the emulsifier is present in the composition in a weight ratio of compound of Formula (I) to the emulsifier of about 1:1. In certain embodiments, the emulsifier is present in the composition in a weight ratio of compound of Formula (I) to the emulsifier of about 1:1.5. In certain embodiments, the emulsifier is present in the composition in a weight ratio of compound of Formula (I) to the emulsifier of about 1:2. In certain embodiments, the emulsifier is present in the composition in a weight ratio of compound of Formula (I) to the emulsifier of about 1:3 to about 1:7. In certain embodiments, the emulsifier is present in the composition in a weight ratio of compound of Formula (I) to the emulsifier of about 1:3. In certain embodiments, the emulsifier is present in the composition in a weight ratio of compound of Formula (I) to the emulsifier of about 1:4. In certain embodiments, the emulsifier is present in the composition in a weight ratio of compound of Formula (I) to the emulsifier of about 1:5. In certain embodiments, the emulsifier is present in the composition in a weight ratio of compound of Formula (I) to the emulsifier of about 1:6. In certain embodiments, the emulsifier is present in the composition in a weight ratio of compound of Formula (I) to the emulsifier of about 1:7.

In certain embodiments, the pharmaceutical composition further comprises a solubilizer.

In certain embodiments, the solubilizer is present in the composition in a weight ratio of compound of Formula (I) to solubilizer of about 1:1 to about 1:5 (e.g., about 1:2 to about 1:4, e.g., about 1:3). In certain embodiments, the solubilizer is present in the composition in a weight ratio of compound of Formula (I) to solubilizer of about 1:1. In certain embodiments, the solubilizer is present in the composition in a weight ratio of compound of Formula (I) to solubilizer of about 1:2. In certain embodiments, the solubilizer is present in the composition in a weight ratio of compound of Formula (I) to solubilizer of about 1:3. In certain embodiments, the solubilizer is present in the composition in a weight ratio of compound of Formula (I) to solubilizer of about 1:4. In certain embodiments, the solubilizer is present in the composition in a weight ratio of compound of Formula (I) to solubilizer of about 1:5. In certain embodiments, the solubilizer is present in the composition in a weight ratio of compound of Formula (I) to solubilizer of about 1:4. In certain embodiments, the solubilizer is present in the composition in a weight ratio of compound of Formula (I) to solubilizer of about 1:6. In certain embodiments, the solubilizer is present in the composition in a weight ratio of compound of Formula (I) to solubilizer of about 1:4. In certain embodiments, the solubilizer is present in the composition in a weight ratio of compound of Formula (I) to solubilizer of about 1:7. In certain embodiments, the solubilizer is present in the composition in a weight ratio of compound of Formula (I) to solubilizer of about 1:4. In certain embodiments, the solubilizer is present in the composition in a weight ratio of compound of Formula (I) to solubilizer of about 1:8. In certain embodiments, the solubilizer is present in the composition in a weight ratio of compound of Formula (I) to solubilizer of about 1:4. In certain embodiments, the solubilizer is present in the composition in a weight ratio of compound of Formula (I) to solubilizer of about 1:9. In certain embodiments, the solubilizer is present in the composition in a weight ratio of compound of Formula (I) to solubilizer of about 1:10 to about 1:20 (e.g., about 1:11 to about 1:16). In certain embodiments, the solubilizer is present in the composition in a weight ratio of compound of Formula (I) to solubilizer of about 1:10. In certain embodiments, the solubilizer is present in the composition in a weight ratio of compound of Formula (I) to solubilizer of about 1:11. In certain embodiments, the solubilizer is present in the composition in a weight ratio of compound of Formula (I) to solubilizer of about 1:12. In certain embodiments, the solubilizer is present in the composition in a weight ratio of compound of Formula (I) to solubilizer of about 1:13. In certain embodiments, the solubilizer is present in the composition in a weight ratio of compound of Formula (I) to solubilizer of about 1:14. In certain embodiments, the solubilizer is present in the composition in a weight ratio of compound of Formula (I) to solubilizer of about 1:15. In certain embodiments, the solubilizer is present in the composition in a weight ratio of compound of Formula (I) to solubilizer of about 1:16. In certain embodiments, the solubilizer is present in the composition in a weight ratio of compound of Formula (I) to solubilizer of about 1:17. In certain embodiments, the solubilizer is present in the composition in a weight ratio of compound of Formula (I) to solubilizer of about 1:18. In certain embodiments, the solubilizer is present in the composition in a weight ratio of compound of Formula (I) to solubilizer of about 1:19. In certain embodiments, the solubilizer is present in the composition in a weight ratio of compound of Formula (I) to solubilizer of about 1:20.

In certain embodiments, the pharmaceutical composition further comprises a polyethylene glycol (PEG).

In certain embodiments, the polyethylene glycol is present in the composition in a weight ratio of compound of Formula (I) to polyethylene glycol of about 1:2 to about 1:6 (e.g., about 1:3 to about 1:5, e.g., about 1:4). In certain embodiments, the polyethylene glycol is present in the composition in a weight ratio of compound of Formula (I) to polyethylene glycol of about 1:1. In certain embodiments, the polyethylene glycol is present in the composition in a weight ratio of compound of Formula (I) to polyethylene glycol of about 1:2. In certain embodiments, the polyethylene glycol is present in the composition in a weight ratio of compound of Formula (I) to polyethylene glycol of about 1:3. In certain embodiments, the polyethylene glycol is present in the composition in a weight ratio of compound of Formula (I) to polyethylene glycol of about 1:4. In certain embodiments, the polyethylene glycol is present in the composition in a weight ratio of compound of Formula (I) to polyethylene glycol of about 1:5. In certain embodiments, the polyethylene glycol is present in the composition in a weight ratio of compound of Formula (I) to polyethylene glycol of about 1:6. In certain embodiments, the polyethylene glycol is present in the composition in a weight ratio of compound of Formula (I) to polyethylene glycol of about 1:7. In certain embodiments, the polyethylene glycol is present in the composition in a weight ratio of compound of Formula (I) to polyethylene glycol of about 1:8. In certain embodiments, the polyethylene glycol is present in the composition in a weight ratio of compound of Formula (I) to polyethylene glycol of about 1:9. In certain embodiments, the polyethylene glycol is present in the composition in a weight ratio of compound of Formula (I) to polyethylene glycol of about 1:10. In certain embodiments, the polyethylene glycol is present in the composition in a weight ratio of compound of Formula (I) to polyethylene glycol of about 1:11. In certain embodiments, the polyethylene glycol is present in the composition in a weight ratio of compound of Formula (I) to polyethylene glycol of about 1:12 to about 1:20 (e.g., about 1:15 to about 1:17). In certain embodiments, the polyethylene glycol is present in the composition in a weight ratio of compound of Formula (I) to polyethylene glycol of about 1:12. In certain embodiments, the polyethylene glycol is present in the composition in a weight ratio of compound of Formula (I) to polyethylene glycol of about 1:13. In certain embodiments, the polyethylene glycol is present in the composition in a weight ratio of compound of Formula (I) to polyethylene glycol of about 1:14. In certain embodiments, the polyethylene glycol is present in the composition in a weight ratio of compound of Formula (I) to polyethylene glycol of about 1:15. In certain embodiments, the polyethylene glycol is present in the composition in a weight ratio of compound of Formula (I) to polyethylene glycol of about 1:16. In certain embodiments, the polyethylene glycol is present in the composition in a weight ratio of compound of Formula (I) to polyethylene glycol of about 1:17. In certain embodiments, the polyethylene glycol is present in the composition in a weight ratio of compound of Formula (I) to polyethylene glycol of about 1:18. In certain embodiments, the polyethylene glycol is present in the composition in a weight ratio of compound of Formula (I) to polyethylene glycol of about 1:19. In certain embodiments, the polyethylene glycol is present in the composition in a weight ratio of compound of Formula (I) to polyethylene glycol of about 1:20.

In certain embodiments, the pharmaceutical composition further comprises a surfactant.

In certain embodiments, the surfactant is present in the composition in a weight ratio of compound of Formula (I) to surfactant of about 2:1 to about 1:2 (e.g., about 1:1 to about 1:2, e.g. about 1:2). In certain embodiments, the surfactant is present in the composition in a weight ratio of compound of Formula (I) to surfactant of about 4:1. In certain embodiments, the surfactant is present in the composition in a weight ratio of compound of Formula (I) to surfactant of about 3:1. In certain embodiments, the surfactant is present in the composition in a weight ratio of compound of Formula (I) to surfactant of about 2:1. In certain embodiments, the surfactant is present in the composition in a weight ratio of compound of Formula (I) to surfactant of about 1:2. In certain embodiments, the surfactant is present in the composition in a weight ratio of compound of Formula (I) to surfactant of about 1:2 to about 1:6 (e.g., about 1:3 to about 1:5). In certain embodiments, the surfactant is present in the composition in a weight ratio of compound of Formula (I) to surfactant of about 1:2. In certain embodiments, the surfactant is present in the composition in a weight ratio of compound of Formula (I) to surfactant of about 1:3. In certain embodiments, the surfactant is present in the composition in a weight ratio of compound of Formula (I) to surfactant of about 1:4. In certain embodiments, the surfactant is present in the composition in a weight ratio of compound of Formula (I) to surfactant of about 1:5. In certain embodiments, the surfactant is present in the composition in a weight ratio of compound of Formula (I) to surfactant of about 1:6.

In certain embodiments, the pharmaceutical composition further comprises an antioxidant.

In certain embodiments, the antioxidant is present in the composition in a weight ratio of compound of Formula (I) to antioxidant of about 10:1 to about 30:1 (e.g., about 15:1 to about 25:1, e.g., about 20:1. In certain embodiments, the antioxidant is present in the composition in a weight ratio of compound of Formula (I) to antioxidant of about 21:1. In certain embodiments, the antioxidant is present in the composition in a weight ratio of compound of Formula (I) to antioxidant of about 22:1. In certain embodiments, the antioxidant is present in the composition in a weight ratio of compound of Formula (I) to antioxidant of about 23:1. In certain embodiments, the antioxidant is present in the composition in a weight ratio of compound of Formula (I) to antioxidant of about 24:1. In certain embodiments, the antioxidant is present in the composition in a weight ratio of compound of Formula (I) to antioxidant of about 25:1. In certain embodiments, the antioxidant is present in the composition in a weight ratio of compound of Formula (I) to antioxidant of about 26:1. In certain embodiments, the antioxidant is present in the composition in a weight ratio of compound of Formula (I) to antioxidant of about 27:1. In certain embodiments, the antioxidant is present in the composition in a weight ratio of compound of Formula (I) to antioxidant of about 28:1. In certain embodiments, the antioxidant is present in the composition in a weight ratio of compound of Formula (I) to antioxidant of about 29:1. In certain embodiments, the antioxidant is present in the composition in a weight ratio of compound of Formula (I) to antioxidant of about 30:1. In certain embodiments, the antioxidant is present in the composition in a weight ratio of compound of Formula (I) to antioxidant of about 2:1 to about 20:1 (e.g., about 5:1). In certain embodiments, the antioxidant is present in the composition in a weight ratio of compound of Formula (I) to antioxidant of about 2:1. In certain embodiments, the antioxidant is present in the composition in a weight ratio of compound of Formula (I) to antioxidant of about 3:1. In certain embodiments, the antioxidant is present in the composition in a weight ratio of compound of Formula (I) to antioxidant of about 4:1. In certain embodiments, the antioxidant is present in the composition in a weight ratio of compound of Formula (I) to antioxidant of about 5:1. In certain embodiments, the antioxidant is present in the composition in a weight ratio of compound of Formula (I) to antioxidant of about 6:1. In certain embodiments, the antioxidant is present in the composition in a weight ratio of compound of Formula (I) to antioxidant of about 7:1. In certain embodiments, the antioxidant is present in the composition in a weight ratio of compound of Formula (I) to antioxidant of about 8:1. In certain embodiments, the antioxidant is present in the composition in a weight ratio of compound of Formula (I) to antioxidant of about 9:1. In certain embodiments, the antioxidant is present in the composition in a weight ratio of compound of Formula (I) to antioxidant of about 10:1. In certain embodiments, the antioxidant is present in the composition in a weight ratio of compound of Formula (I) to antioxidant of about 11:1. In certain embodiments, the antioxidant is present in the composition in a weight ratio of compound of Formula (I) to antioxidant of about 12:1. In certain embodiments, the antioxidant is present in the composition in a weight ratio of compound of Formula (I) to antioxidant of about 13:1. In certain embodiments, the antioxidant is present in the composition in a weight ratio of compound of Formula (I) to antioxidant of about 14:1. In certain embodiments, the antioxidant is present in the composition in a weight ratio of compound of Formula (I) to antioxidant of about 15:1. In certain embodiments, the antioxidant is present in the composition in a weight ratio of compound of Formula (I) to antioxidant of about 16:1. In certain embodiments, the antioxidant is present in the composition in a weight ratio of compound of Formula (I) to antioxidant of about 17:1. In certain embodiments, the antioxidant is present in the composition in a weight ratio of compound of Formula (I) to antioxidant of about 18:1. In certain embodiments, the antioxidant is present in the composition in a weight ratio of compound of Formula (I) to antioxidant of about 19:1. In certain embodiments, the antioxidant is present in the composition in a weight ratio of compound of Formula (I) to antioxidant of about 20:1.

In certain embodiments, provided herein is a composition or formulation as set forth in Table 1 (or oral dosage form comprising (e.g., dosage form comprising a capsule containing) such a composition or formulation) (e.g., wherein the total wt. % does not exceed 100%).

TABLE 1

Exemplary Compositions

| Component | Formulation 1 (% w/w) | Formulation 2 (% w/w) | Formulation 3 (% w/w) |
|---|---|---|---|
| Solubilizer | 15-50 | 20-40 | 25-30 |
| Solvent or Cosolvent(s) (e.g., PEG) | 15-50 | 25-50 | 35-40 |
| Surfactant | 5-40 | 5-30 | 8-15 |
| Emulsifier | 5-40 | 5-30 | 10-20 |
| Antioxidant | 0.05-5 | 0.1-3 | 0.2-1 |
| API | >5 | >7 | >8.5 |

In some embodiments, any composition or formulation provided herein comprises a solubilizer, solvent, surfactant, emulsifier, and/or antioxidant in an amount described in Table 1, irrespective of the amount of any other component (which may or may not be present, such as if achieving the beneficial results provided herein) of the composition.

In specific embodiments, provided herein is a composition or formulation comprising the following components in the amounts (e.g., wt. % and/or absolute mass) described in Table 2:

TABLE 2

Exemplary Composition

| Component | % w/w | Amount (e.g., in a 80 mg of compound of Formula (I) dosage form) | Amount (mg/g) |
|---|---|---|---|
| Solubilizer | 27.09 | 236 mg | 270.9 mg |
| PEG | 38.83 | 338 mg | 388.3 mg |
| Surfactant | 10.84 | 94 mg | 108.4 mg |
| Glyceride Emulsifier | 13.54 | 118 mg | 135.4 mg |
| Antioxidant | 0.50 | 4 mg | 5 mg |
| API | 9.20 | 80 mg | 92 mg |

Provided herein, in another aspect, is a pharmaceutical composition comprising:

a. a therapeutically effective amount of a compound of Formula (I):

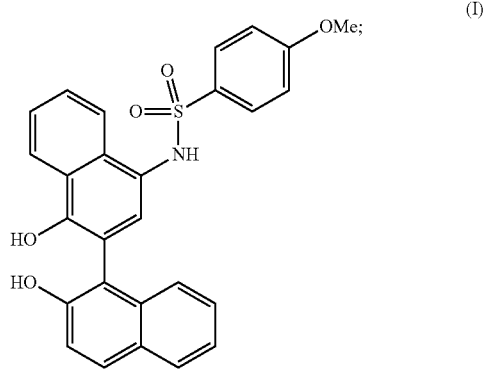 [SMILES: COc1ccc(S(=O)(=O)Nc2cc(-c3c(O)ccc4ccccc34)c(O)c3ccccc23)cc1]

b. an emulsifier (e.g., glyceride), the emulsifier being present in the composition in a % w/w of about 5 to about 40% (e.g., about 5 to about 30%, about 10 to about 20%);

c. a solubilizer, the solubilizer being present in the composition in a % w/w of about 15 to about 50% (e.g., about 20 to about 40%, about 25 to about 30%);

d. a polyethylene glycol (PEG), the polyethylene glycol being present in the composition in a % w/w of about 15 to about 50% (e.g., about 25 to about 50%, about 35 to about 40%);

e. a surfactant, the surfactant being present in the composition in a % w/w of about 5 to about 40% (e.g., about 5 to about 30%, about 8 to about 15%);

f. an antioxidant, the antioxidant being present in the composition in a % w/w of about 0.05 to about 5% (e.g., about 0.1 to about 3%, about 0.2 to about 1%).

In certain embodiments, the composition is or is a part of a self-emulsifying drug dispersion (SEDD). In certain embodiments, the composition is a capsule fill formulation. In certain embodiments, the composition further comprises a capsule shell.

In certain embodiments, the compound of Formula (I) is present in the formulation in a concentration of at least 50 mg/g (e.g., at least 60 mg/g, at least 70 mg/g, at least 80 mg/g, or at least 90 mg/g) (e.g., excluding the mass of a capsule shell). In certain embodiments, the compound of Formula (I) is present in the formulation in a concentration of at least 50 mg/g. In certain embodiments, the compound of Formula (I) is present in the formulation in a concentration of at least 60 mg/g. In certain embodiments, the compound of Formula (I) is present in the formulation in a concentration of at least 70 mg/g. In certain embodiments, the compound of Formula (I) is present in the formulation in a concentration of at least 80 mg/g. In certain embodiments, the compound of Formula (I) is present in the formulation in a concentration of at least 90 mg/g.

In certain embodiments, the compound of Formula (I) is present in the formulation in a concentration of at least 60 mg/mL (e.g., at least 70 mg/mL, at least 80 mg/mL, at least 90 mg/mL, or at least 100 mg/mL) (e.g., excluding the volume of a capsule shell). In certain embodiments, the compound of Formula (I) is present in the formulation in a concentration of at least 60 mg/mL. In certain embodiments, the compound of Formula (I) is present in the formulation in a concentration of at least 70 mg/mL. In certain embodiments, the compound of Formula (I) is present in the formulation in a concentration of at least 80 mg/mL. In certain embodiments, the compound of Formula (I) is present in the formulation in a concentration of at least 90 mg/mL. In certain embodiments, the compound of Formula (I) is present in the formulation in a concentration of at least 100 mg/mL.

In certain embodiments, at least 60 wt. % (e.g., at least 80 wt. %, at least 90 wt. %, or at least 95 wt. %) of the compound of Formula (I) is soluble (dissolved) in the composition. In certain embodiments, at least 60 wt. % of the compound of Formula (I) is soluble (dissolved) in the composition. In certain embodiments, at least 80 wt. % of the compound of Formula (I) is soluble (dissolved) in the composition. In certain embodiments, at least 90 wt. % of the compound of Formula (I) is soluble (dissolved) in the composition. In certain embodiments, at least 95 wt. % of the compound of Formula (I) is soluble (dissolved) in the composition.

Provided herein, in another aspect, is an oral dosage form comprising a pharmaceutical composition, the pharmaceutical composition comprising:

a. at least 40 mg (e.g., at least 50 mg, at least 60 mg, at least 75 mg) of a compound of Formula (I):

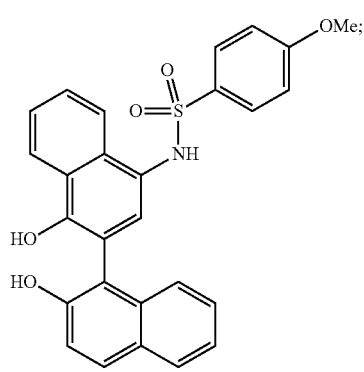

b. an emulsifier (e.g., glyceride), the emulsifier being present in the composition in a % w/w of about 5 to about 40% (e.g., about 5 to about 30%, about 10 to about 20%);
c. a solubilizer, the solubilizer being present in the composition in a % w/w of about 15 to about 50% (e.g., about 20 to about 40%, about 25 to about 30%);
d. a polyethylene glycol (PEG), the polyethylene glycol being present in the composition in a % w/w of about 15 to about 50% (e.g., about 25 to about 50%, about 35 to about 40%);
e. a surfactant, the surfactant being present in the composition in a % w/w of about 5 to about 40% (e.g., about 5 to about 30%, about 8 to about 15%);
f. an antioxidant, the antioxidant being present in the composition in a % w/w of about 0.05 to about 5% (e.g., about 0.1 to about 3%, about 0.2 to about 1%).

Provided herein, in another aspect, is an oral dosage form comprising a pharmaceutical composition, the pharmaceutical composition comprising at least 40 mg (e.g., at least 50 mg, at least 60 mg, or at least 75 mg) of a compound of Formula (I):

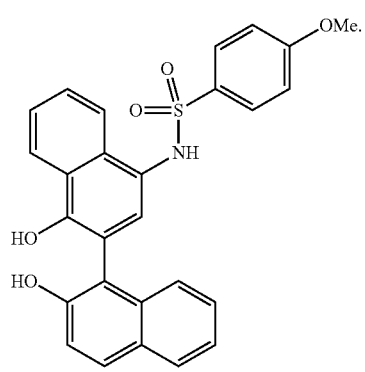

In certain embodiments, the pharmaceutical composition comprises at least 40 mg of a compound of Formula (I). In certain embodiments, the pharmaceutical composition comprises at least 50 mg of a compound of Formula (I). In certain embodiments, the pharmaceutical composition comprises at least 60 mg of a compound of Formula (I). In certain embodiments, the pharmaceutical composition comprises at least 75 mg of a compound of Formula (I).

In certain embodiments, the pharmaceutical composition further comprises an emulsifier (e.g., glyceride). In certain embodiments, the emulsifier is present in the composition in a % w/w of about 5 to about 40% (e.g., about 5 to about 30%, about 10 to about 20%, about 10% to about 15%). In certain embodiments, the emulsifier is present in the composition in a % w/w of about 5%. In certain embodiments, the emulsifier is present in the composition in a % w/w of about 10%. In certain embodiments, the emulsifier is present in the composition in a % w/w of about 15%. In certain embodiments, the emulsifier is present in the composition in a % w/w of about 20%. In certain embodiments, the emulsifier is present in the composition in a % w/w of about 25%. In certain embodiments, the emulsifier is present in the composition in a % w/w of about 30%. In certain embodiments, the emulsifier is present in the composition in a % w/w of about 35%. In certain embodiments, the emulsifier is present in the composition in a % w/w of about 40%.

In certain embodiments, the pharmaceutical composition further comprises a solubilizer. In certain embodiments, the solubilizer is present in the composition in a % w/w of about 15 to about 50% (e.g., about 20 to about 40%, about 25 to about 30%). In certain embodiments, the solubilizer is present in the composition in a % w/w of about 15%. In certain embodiments, the solubilizer is present in the composition in a % w/w of about 20%. In certain embodiments, the solubilizer is present in the composition in a % w/w of about 25%. In certain embodiments, the solubilizer is present in the composition in a % w/w of about 30%. In certain embodiments, the solubilizer is present in the composition in a % w/w of about 35%. In certain embodiments, the solubilizer is present in the composition in a % w/w of about 40%. In certain embodiments, the solubilizer is present in the composition in a % w/w of about 45%. In certain embodiments, the solubilizer is present in the composition in a % w/w of about 50%.

In certain embodiments, the pharmaceutical composition further comprises a polyethylene glycol (PEG). In certain embodiments, the polyethylene glycol is present in the composition in a % w/w of about 15 to about 50% (e.g., about 25 to about 50%, about 35 to about 40%). In certain embodiments, the polyethylene glycol is present in the composition in a % w/w of about 15%. In certain embodiments, the polyethylene glycol is present in the composition in a % w/w of about 20%. In certain embodiments, the polyethylene glycol is present in the composition in a % w/w of about 25%. In certain embodiments, the polyethylene glycol is present in the composition in a % w/w of about 30%. In certain embodiments, the polyethylene glycol is present in the composition in a % w/w of about 35%. In certain embodiments, the polyethylene glycol is present in the composition in a % w/w of about 40%. In certain embodiments, the polyethylene glycol is present in the composition in a % w/w of about 45%. In certain embodiments, the polyethylene glycol is present in the composition in a % w/w of about 50%.

In certain embodiments, the pharmaceutical composition further comprises a surfactant. In certain embodiments, the surfactant is present in the composition in a % w/w of about 5 to about 40% (e.g., about 5 to about 30%, about 8 to about 15%). In certain embodiments, the surfactant is present in the composition in a % w/w of about 5%. In certain embodiments, the surfactant is present in the composition in a % w/w of about 8%. In certain embodiments, the surfactant is present in the composition in a % w/w of about 9%. In certain embodiments, the surfactant is present in the composition in a % w/w of about 10%. In certain embodiments, the surfactant is present in the composition in a % w/w of about 11%. In certain embodiments, the surfactant is present in the composition in a % w/w of about 12%. In certain embodiments, the surfactant is present in the composition in a % w/w of about 15%.

In certain embodiments, the pharmaceutical composition further comprises an antioxidant. In certain embodiments, the antioxidant is present in the composition in a % w/w of about 0.05 to about 5% (e.g., about 0.1 to about 3%, about 0.2 to about 1%). In certain embodiments, the antioxidant is present in the composition in a % w/w of about 0.05%. In certain embodiments, the antioxidant is present in the composition in a % w/w of about 0.1%. In certain embodiments, the antioxidant is present in the composition in a % w/w of about 0.2%. In certain embodiments, the antioxidant is present in the composition in a % w/w of about 0.3%. In certain embodiments, the antioxidant is present in the composition in a % w/w of about 0.4%. In certain embodiments, the antioxidant is present in the composition in a % w/w of about 0.5%. In certain embodiments, the antioxidant is present in the composition in a % w/w of about 0.6%. In certain embodiments, the antioxidant is present in the composition in a % w/w of about 0.7%. In certain embodiments, the antioxidant is present in the composition in a % w/w of about 0.8%. In certain embodiments, the antioxidant is present in the composition in a % w/w of about 0.9%. In certain embodiments, the antioxidant is present in the composition in a % w/w of about 1%. In certain embodiments, the antioxidant is present in the composition in a % w/w of about 2%. In certain embodiments, the antioxidant is present in the composition in a % w/w of about 3%. In certain embodiments, the antioxidant is present in the composition in a % w/w of about 4%. In certain embodiments, the antioxidant is present in the composition in a % w/w of about 5%.

In certain embodiments, the composition is as described in any of the previously described embodiments.

Provided in certain embodiments herein is a method of treating fibrosis, cancer, or chronic inflammation in an individual in need thereof, the method comprising administering to the individual any composition, formulation, or oral dosage described herein.

Provided herein, in another aspect, is a method of treating fibrosis, cancer, or chronic inflammation in an individual in need thereof, the method comprising administering to the individual a high dose of a compound of Formula (I):

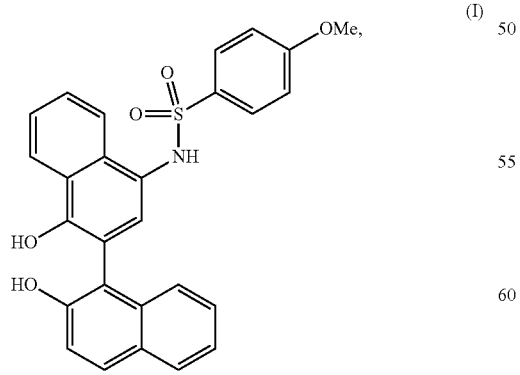

the high dose of the compound of Formula (I) comprising administration of at least 15 mg/kg/day of the compound of Formula (I) to the individual.

In certain embodiments, the method comprises administering the compound of Formula (I) in a total of no more than 25 oral dosage forms per day. In certain embodiments, the method comprises administering the compound of Formula (I) in a total of no more than 0.3 oral dosage forms per 1 kg of mass of the individual per day. In certain embodiments, the method comprises administering the compound of Formula (I) in a total of no more than 0.35 oral dosage forms per 1 kg of mass of the individual per day.

Provided herein, in another aspect, is a method of treating fibrosis, cancer, or chronic inflammation in an individual in need thereof, the method comprising administering to the individual a plurality of oral dosage forms, the plurality of oral dosage forms collectively comprising therapeutically effective amount of a compound of Formula (I):

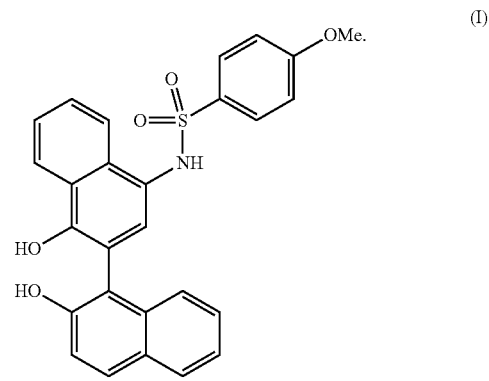 [SMILES: COc1ccc(S(=O)(=O)Nc2cc(-c3c(O)ccc4ccccc34)c(O)c3ccccc23)cc1]

Provided herein, in another aspect, is a method of treating fibrosis, cancer, or chronic inflammation in an individual in need thereof, the method comprising administering to the individual a plurality of oral dosage forms, the plurality of oral dosage forms collectively comprising therapeutically effective amount of a compound of Formula (I):

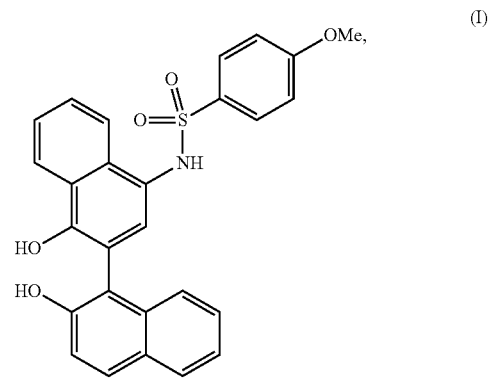 [SMILES: COc1ccc(S(=O)(=O)Nc2cc(-c3c(O)ccc4ccccc34)c(O)c3ccccc23)cc1]

the plurality of oral dosage forms comprising no more than 0.35 oral dosage forms for every 1 kg of mass of the individual per day (e.g., on average or maximum).

In certain embodiments, a cancer treated according to a method provided herein is a liver cancer, lung cancer, head and neck cancer, breast cancer, skin cancer, kidney cancer, testicular cancer, colon cancer, rectal cancer, gastric cancer, metastatic melanoma, prostate cancer, ovarian cancer, cervical cancer, bone cancer, spleen cancer, gall bladder cancer, brain cancer, pancreatic cancer, stomach cancer, anal cancer, prostate cancer, multiple myeloma, post-transplant lymphoproliferative disease, restenosis, myelodysplastic syndrome, leukemia, lymphoma, or acute myelogenous leukemia. In some embodiments, a cancer treated according to a method provided herein is a liver cancer, lung cancer, hepatocellular carcinoma, head and neck squamous cell carcinoma, non-small cell lung cancer, or estrogen receptor-positive breast cancer. In some embodiments, a cancer treated according to a method provided herein is head and neck cancer, lung cancer, liver cancer, breast cancer, ovarian cancer, colon cancer, multiple myeloma, leukemia, or pancreatic cancer. In some embodiments, the leukemia is acute myelogenous leukemia.

In some embodiments, chronic inflammation treated herein is inflammatory bowel disease (IBD), ulcerative colitis, Crohn's disease, asthma, anaphylaxis, cancer cachexia, chronic kidney disease cachexia, nonalcoholic steatohepatitis (NASH), psoriasis, uveitis, scleritis, multiple sclerosis, or pancreatitis. In some embodiments, chronic inflammation treated herein is inflammatory bowel disease (IBD), ulcerative colitis, Crohn's disease, asthma, anaphylaxis, cancer cachexia, chronic kidney disease cachexia, or nonalcoholic steatohepatitis (NASH). In some embodiments, the anaphylaxis comprises anaphylactic shock.

In certain embodiments, the fibrosis is skin fibrosis (or dermal fibrosis), cardiac fibrosis, cirrhosis, pulmonary fibrosis, bone marrow fibrosis, intestine fibrosis, pancreatic fibrosis, joint fibrosis, liver fibrosis, retroperitoneum, renal fibrosis, myelofibrosis, non-alcoholic fatty liver disease, steatohepatitis, systemic sclerosis (including diffuse systemic sclerosis or limited systemic sclerosis), endomyocardial fibrosis, myocardial infarction, atrial fibrosis, mediastinal fibrosis, progressive massive fibrosis, nephrogenic systemic fibrosis, Keloid, arthrofibrosis, adhesive capsulitis, or cystic fibrosis. In certain embodiments, the fibrosis is skin fibrosis (scleroderma), cardiac fibrosis, cirrhosis, pulmonary fibrosis, bone marrow fibrosis, intestine fibrosis, pancreatic fibrosis, joint fibrosis, liver fibrosis, retroperitoneum, myelofibrosis, non-alcoholic fatty liver disease, steatohepatitis, or systemic sclerosis. In certain embodiments, the fibrosis is skin fibrosis (scleroderma), cardiac fibrosis, cirrhosis, or pulmonary fibrosis.

In certain embodiments, the fibrosis is fibrosis following exposure to certain drugs such as chemotherapy, fibrosis following exposure to environmental or other toxins or allergens, fibrosis occurring after an ischemia/reperfusion injury such as myocardial infarction or hypotension, fibrosis occurring after radiation, fibrosis following hepatitis induced by alcohol, toxins, drugs or infections, primary biliary cirrhosis, fibrosis following viral infections involving the heart, liver, or lung, and/or idiopathic retroperitoneal fibrosis.

In certain embodiments, any method provided herein is a method of treating muscle wasting, muscle weakness, or cachexia. The muscle weakness and/or muscle wasting and/or cachexia may have an unknown cause or it may be associated with an underlying condition. The underlying condition may be a catabolic condition. In some embodiments, the underlying medical condition associated with cachexia is least renal failure, cancer, AIDS, HIV infection, chronic obstructive lung disease (including emphysema), multiple sclerosis, congestive heart failure, tuberculosis, familial amyloid polyneuropathy, acrodynia, hormonal deficiency, metabolic acidosis, infectious disease, chronic pancreatitis, autoimmune disorder, celiac disease, Crohn's disease, electrolyte imbalance, Addison's disease, sepsis, burns, trauma, fever, long bone fracture, hyperthyroidism, prolonged steroid therapy, surgery, bone marrow transplant, atypical pneumonia, brucellosis, endocarditis, Hepatitis B, lung abscess, mastocytosis, paraneoplastic syndrome, polyarteritis nodosa, sarcoidosis, systemic lupus erythematosus, myositis, polymyositis, dematomyosytis, rheumatological diseases, autoimmune disease, collagen-vascular disease, visceral leishmaniasis, prolonged bed rest, and/or addiction to drugs, such as amphetamine, opiates, or barbitutates.

In certain embodiments, any method provided herein is a method of treating, preventing, or reducing the risk or severity of an allergic reaction. In some embodiments, the allergic reaction is induced following an exposure to an allergen. In some embodiments, the allergen is a food allergen (such as milk, legumes, shellfish, tree nuts, eggs, fish, soy, and wheat), an environmental allergen or seasonal allergen (such as pollen or mold), a venom allergen (such as from wasp, bee, ant, hornet, yellow jacket, or asp), a medication allergen (such as anesthetics, β-lactam antibiotics, aspirin, non-steroidal anti-inflammatory drug, chemotherapy, vaccine, protamine, or herbal preparations), or latex. In some embodiments, the allergic reaction is anaphylaxis, anaphylactic shock, allergic rhinitis, urticaria, food allergy, drug allergy, hymenoptera allerga, bronchial constriction, asthma, or eczema.

In certain embodiments, any method provided herein is a method of treating a viral infection. In some embodiments, the viral infection is a chronic viral infection. In some embodiments, the chronic viral infection is AIDS, HIV infection, Hepatitis B infection, Hepatitis C virus infection, or Epstein-Barr virus infection.

In certain embodiments, any method provided herein is a method of treating graft-versus-host diseases, pulmonary lymphangioleiomyomatosis, chagasic cardiomyopathy, age-related macular degeneration, amyloidosis, astrogliosis in Alzheimer's or other neurodegenerative diseases, or familial amyloid polyneuropathy.

In certain embodiments, any method provided herein is a method of treating a neurodegenerative disease. In some embodiments, the neurodegenerative disease is chemotherapy-induced peripheral neuropathy, diabetic neuropathy, or chemobrain.

In certain embodiments, any method provided herein is a method of treating or reducing the risk or severity of insulin resistance. In some embodiments, the insulin resistance is a result of an underlying condition. In some embodiments, the insulin resistance is associated with muscle of the individual being treated. In some embodiments, the insulin resistance is caused by any reason for the individual, such as elevated free fatty acids in the blood, obesity, being overweight, having visceral fat, having a high fructose intake, having inflammation, being inactive, dysbiosis of the gut microbiota, and/or being genetically predisposed. In certain embodiments, any method provided herein is a method of treating or reducing the risk or severity of medical conditions associated with insulin resistance or that are complications of insulin resistance at least in part, such as severe high blood sugar; severe low blood sugar; heart attack; stroke; kidney disease (including chronic, for example, chronic kidney disease (CKD)); eye problems; cancer; non-alcoholic fatty liver disease (NAFLD); polycystic ovarian syndrome (PCOS); metabolic syndrome; diabetes; or Alzheimer's disease, for example. In certain embodiments, the insulin resistance is a hallmark of metabolic syndrome and type 2 diabetes. Metabolic syndrome is a group of risk factors associated with type 2 diabetes and heart disease. Its symptoms include high blood triglycerides, blood pressure, belly fat, and blood sugar, as well as low HDL (good) cholesterol levels.

In some embodiments, higher or lower pill burden is tolerated. For example, in some embodiments, no more than 1 oral dosage forms for every 1 kg of mass of the individual is administered per day (e.g., on average or maximum). In specific embodiments, no more than 0.8 oral dosage forms for every 1 kg of mass of the individual is administered per day (e.g., on average or maximum). In more specific embodiments, no more than 0.6 oral dosage forms for every 1 kg of mass of the individual is administered per day (e.g., on average or maximum). In still more specific embodiments, no more than 0.5 oral dosage forms for every 1 kg of mass of the individual is administered per day (e.g., on average or maximum). In yet more specific embodiments, no more than 0.4 oral dosage forms for every 1 kg of mass of the individual is administered per day (e.g., on average or maximum). In specific embodiments, no more than 0.3 oral dosage forms for every 1 kg of mass of the individual is administered per day (e.g., on average or maximum). In certain embodiments, lower (e.g., daily) doses of compounds of Formula (I) and/or lower pill burden are required in non-cancer therapies, such as in therapies for fibrosis and/or chronic inflammation. In some embodiments, no more than 0.2 oral dosage forms for every 1 kg of mass of the individual is administered per day (e.g., on average or maximum). In specific embodiments, no more than 0.1 oral dosage forms for every 1 kg of mass of the individual is administered per day (e.g., on average or maximum).

In some embodiments, the pill burden discussed herein is associated with any suitable therapeutic (e.g., daily) dose of compound of Formula (I) and/or loading of compound of Formula (I) in the oral dosage form(s), such as any dose or amount described herein.

For example, in some embodiments, an oral dosage form provided herein comprises any suitable amount of a compound of Formula (I), such as formulated according to any pharmaceutical composition described herein. In some embodiments, an oral dosage form provided herein comprises at least 30 mg of a compound of Formula (I). In specific embodiments, an oral dosage form provided herein comprises at least 40 mg of a compound of Formula (I). In more specific embodiments, an oral dosage form provided herein comprises at least 50 mg of a compound of Formula (I). In still more specific embodiments, an oral dosage form provided herein comprises at least 60 mg of a compound of Formula (I). In yet more specific embodiments, an oral dosage form provided herein comprises at least 70 mg of a compound of Formula (I). In specific embodiments, an oral dosage form provided herein comprises at least 80 mg of a compound of Formula (I).

In certain embodiments, the method comprises administering at least 10 mg/kg/day of the compound of Formula (I) to the individual. In certain embodiments, the method comprises administering at least 15 mg/kg/day of the compound of Formula (I) to the individual. In certain embodiments, the method comprises administering at least 20 mg/kg/day of the compound of Formula (I) to the individual. In certain embodiments, the method comprises administering at least 25 mg/kg/day of the compound of Formula (I) to the individual.

Provided herein, in another aspect, is a method of providing to an individual an improved $C_{max}$ or $AUC_{0-\infty}$ of a compound of Formula (I):

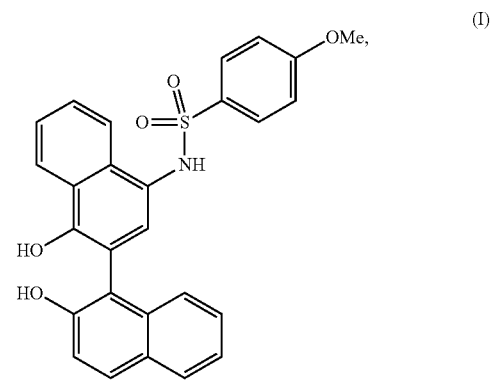 [SMILES: COc1ccc(S(=O)(=O)Nc2cc(-c3c(O)ccc4ccccc34)c(O)c3ccccc23)cc1]

the improved $C_{max}$ or $AUC_{0-\infty}$ being at least 1.1 greater than the effect obtained by administering an otherwise identical amount of a compound of Formula (I) in a formulation of PEG400 and Labrasol®.

In certain embodiments, the method has an administration protocol of any of the previously described embodiments. In certain embodiments, the compound of Formula (I) is administered in a pharmaceutical composition or in one or more oral dosage forms of any of the previously described embodiments.

In certain embodiments, the compound of Formula (I) is administered in any suitable amount. In certain embodiments, the compound of Formula (I) is administered in any suitable dosing interval. In certain embodiments, the compound of Formula (I) is administered once daily. In certain embodiments, the compound of Formula (I) is administered twice daily.

The following references illustrate the efficacy of the compound of Formula (I) in certain therapies described herein and are incorporated by reference in their entirety: Jung et al., *Clin. Cancer Res.* 2017, 23(18), 5537-5546; Bharadwaj et al., *Oncotarget* 2016, 7(18), 26307-26330; Lewis et al., *Lung Cancer* 2015, 90(2), 182-190; Kettner et al., *Clin. Cancer Res.* 2019, 25(13), 3996-4013; Gavino et al., *Allergy* 2016, 71(12), 1684-1692; Hox et al., *J. Allergy Clin. Immunol.* 2016, 138(1), 187-199; Silva et al., *J. Biol. Chem.* 2015, 290(17), 11177-11187; Zhang et al., *Cell Metab.* 2013, 18(3), 368-379; Pedroza et al., *Rheumatology* 2018, 57(10), 1838-1850; and Pedroza et al., *The FASEB Journal* 2016, 30(1), 129-140.

Provided herein, in another aspect, is a crystalline form of a compound of Formula (I).

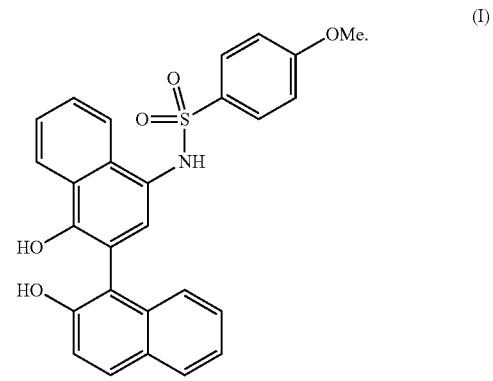 [SMILES: COc1ccc(S(=O)(=O)Nc2cc(-c3c(O)ccc4ccccc34)c(O)c3ccccc23)cc1]

In certain embodiments, the crystalline form is characterized by an X-ray powder diffraction pattern comprising peaks at 8.1±0.2°, 16.5±0.2°, 18.4±0.2°, 21.8±0.2°, and 22.6±0.2° two theta.

In certain embodiments, the X-ray powder diffraction pattern further comprises at least one peak selected from 9.6±0.2°, 11.4±0.2°, 12.7±0.2°, and 14.7±0.2° two theta. In certain embodiments, the X-ray powder diffraction pattern further comprises at least two peaks selected from 9.6±0.2°, 11.4±0.2°, 12.7±0.2°, and 14.7±0.2° two theta. In certain embodiments, the X-ray powder diffraction pattern further comprises at least three peaks selected from 9.6±0.2°, 11.4 0.2°, 12.7±0.2°, and 14.7±0.2° two theta. In certain embodiments, the X-ray powder diffraction pattern further comprises peaks at 9.6±0.2°, 11.4±0.2°, 12.7±0.2°, and 14.7±0.2° two theta.

In certain embodiments, the X-ray powder diffraction pattern further comprises at least one peak selected from 19.7±0.2°, 20.2±0.2°, 20.8±0.2°, and 24.4±0.2° two theta. In certain embodiments, the X-ray powder diffraction pattern further comprises at least two peaks selected from 19.7±0.2°, 20.2±0.2°, 20.8±0.2°, and 24.4±0.2° two theta. In certain embodiments, the X-ray powder diffraction pattern further comprises at least three peaks selected from 19.7±0.2°, 20.2±0.2°, 20.8±0.2°, and 24.4±0.2° two theta. In certain embodiments, the X-ray powder diffraction pattern further comprises peaks at 19.7±0.2°, 20.2±0.2°, 20.8±0.2°, and 24.4±0.2° two theta.

In certain embodiments, the X-ray powder diffraction pattern further comprises at least one peak selected from 26.1±0.2°, 29.3±0.2°, and 30.7±0.2° two theta. In certain embodiments, the X-ray powder diffraction pattern further comprises at least two peaks selected from 26.1±0.2°, 29.3±0.2°, and 30.7±0.2° two theta. In certain embodiments, the X-ray powder diffraction pattern further comprises peaks at 26.1±0.2°, 29.3±0.2°, and 30.7±0.2° two theta.

In certain embodiments, the crystalline form is characterized by an X-ray powder diffraction pattern comprising peaks at 8.1±0.2°, 9.6±0.2°, 11.4±0.2°, 12.7±0.2°, 14.7±0.2°, 16.5±0.2°, 18.4±0.2°, from 19.7±0.2°, 20.2±0.2°, 20.8±0.2°, 21.8±0.2°, 22.6±0.2°, 24.4±0.2°, 26.1±0.2°, 29.3±0.2°, and 30.7±0.2° two theta.

In certain embodiments, the crystalline form is characterized by an X-ray powder diffraction pattern comprising peaks at 8.13±0.2°, 16.50±0.2°, 18.41±0.2°, 21.77±0.2°, and 22.64±0.2° two theta.

In certain embodiments, the X-ray powder diffraction pattern further comprises at least one peak selected from 9.56±0.2°, 11.43±0.2°, 12.75±0.2°, and 14.66±0.2° two theta. In certain embodiments, the X-ray powder diffraction pattern further comprises at least two peaks selected from 9.56±0.2°, 11.43±0.2°, 12.75±0.2°, and 14.66±0.2° two theta. In certain embodiments, the X-ray powder diffraction pattern further comprises at least three peaks selected from 9.56±0.2°, 11.43±0.2°, 12.75±0.2°, and 14.66±0.2° two theta. In certain embodiments, the X-ray powder diffraction pattern further comprises peaks at 9.56±0.2°, 11.43±0.2°, 12.75±0.2°, and 14.66±0.2° two theta.

In certain embodiments, the X-ray powder diffraction pattern further comprises at least one peak selected from 19.70±0.2°, 20.21±0.2°, 20.81±0.2°, and 24.43±0.2° two theta. In certain embodiments, the X-ray powder diffraction pattern further comprises at least two peaks selected from 19.70±0.2°, 20.21±0.2°, 20.81±0.2°, and 24.43±0.2° two theta. In certain embodiments, the X-ray powder diffraction pattern further comprises at least three peaks selected from 19.70±0.2°, 20.21±0.2°, 20.81±0.2°, and 24.43±0.2° two theta. In certain embodiments, the X-ray powder diffraction pattern further comprises peaks at 19.70±0.2°, 20.21±0.2°, 20.81±0.2°, and 24.43±0.2° two theta.

In certain embodiments, the X-ray powder diffraction pattern further comprises at least one peak selected from 26.10±0.2°, 29.29±0.2°, and 30.75±0.2° two theta. In certain embodiments, the X-ray powder diffraction pattern further comprises at least two peaks selected from 26.10±0.2°, 29.29±0.2°, and 30.75±0.2° two theta. In certain embodiments, the X-ray powder diffraction pattern further comprises peaks at 26.10±0.2°, 29.29±0.2°, and 30.75±0.2° two theta.

In certain embodiments, the crystalline form is characterized by an X-ray powder diffraction pattern comprising peaks at 8.13±0.2°, 9.56±0.2°, 11.43±0.2°, 12.75±0.2°, 14.66±0.2°, 16.50±0.2°, 18.41±0.2°, from 19.70±0.2°, 20.21±0.2°, 20.81±0.2°, 21.77±0.2°, 22.64±0.2°, 24.43±0.2°, 26.10±0.2°, 29.29±0.2°, and 30.75±0.2° two theta.

In certain embodiments, the crystalline form is characterized by an X-ray powder diffraction pattern substantially as set forth in FIG. 1.

EXAMPLES

Example 1: Two-Component Formulation System

A formulation of the compound dissolved in Labrasol®/PEG400 (60:40) and encapsulated into a hard gelatin capsule (unit dose: 36 mg), while showing encouraging results in 3 dose cohorts, was prevented from advancing to a fourth patient cohort (25.6 mg/kg/day as 12.8 mg/kg twice daily (BID) doses) because of an unacceptably high pill burden. For example, a 70 kg subject in Cohort 4 would require 60 capsules per day split into BID doses.

In order to reduce the pill burden and allow the further therapeutic development of the compound of Formula (I), a second-generation formulation was developed. This formulation contains 80 mg of the compound of Formula (I) per capsule. The 80 mg strength will reduce capsule burden approximately 2.7-fold; the 70 kg subject in Cohort 4 would take 22 capsules per day split into BID doses. The formulation comprises the compound of Formula (I), Kolliphor® RH 40 (PEG-40 hydrogenated castor oil), PEG600, Polysorbate 20, Labrasol®, and citric acid.

Example 2: Multiple-Component Formulations

Solubility of a compound of Formula (I) was evaluated in various excipient combinations set forth in Table 3 below. To determine solubility, an excess amount of the compound of Formula (I) was added to pre-mixed excipient combinations (according to the relative ratio of the excipients as shown in Table 3) and agitated on a shaker protected from light for 2 days at room temperature for liquid excipient combinations. For semi-solid mixtures, the agitation was conducted at 50° C. for 2 days. After 2 days, the samples were centrifuged at 14,000 rpm for 10 minutes, and the supernatants were collected to assess the solubility of a compound of Formula (I) (concentration) in the various excipient combinations by high performance liquid chromatograph (HPLC). The resulting concentrations of the compound of Formula (I) are summarized in Table 3:

TABLE 3

Solubility of the Compound of Formula (I) in Various Formulations

| Excipient mixture # | Excipients | Ratio w % | Compound of Formula (I) Concentration (mg/g) |
|---|---|---|---|
| 1 | Labrasol ® | 30 | 69.2 |
|   | Kolliphor ® RH40 | 45 |   |
|   | PEG 600 | 15 |   |
|   | Polysorbate 80 | 10 |   |
| 2 | Labrasol ® | 20 | 94.3 |
|   | Kolliphor ® RH40 | 45 |   |
|   | PEG 600 | 15 |   |
|   | Polysorbate 80 | 10 |   |
|   | Transcutol ® HP | 10 |   |
| 3 | Labrasol ® | 30 | 77.5 |
|   | Gelucire ® 48/16 | 45 |   |
|   | PEG 600 | 15 |   |
|   | Polysorbate 80 | 10 |   |
| 4 | Labrasol ® | 30 | 57.1 |
|   | Gelucire ® 44/14 | 45 |   |
|   | PEG 600 | 15 |   |
|   | Polysorbate 80 | 10 |   |
| 5 | Kolliphor ® RH40 | 45 | 63.2 |
|   | PEG 600 | 15 |   |
|   | Polysorbate 80 | 10 |   |
|   | Propylene glycol | 30 |   |
| 6 | Labrasol ® | 30 | 95.2 |
|   | Kolliphor ® RH40 | 45 |   |
|   | PEG 600 | 15 |   |
|   | Polysorbate 20 | 10 |   |
| 7 | Kolliphor ® RH40 | 45 | 86.2 |
|   | PEG 600 | 35 |   |
|   | Polysorbate 20 | 10 |   |
|   | Transcutol ® HP | 10 |   |
| 8 | Kolliphor ® RH40 | 45 | 82.5 |
|   | PEG 600 | 30 |   |
|   | Polysorbate 20 | 10 |   |
|   | Labrasol ® | 15 |   |
| 9 | Kolliphor ® RH40 | 30 | 93.0 |
|   | PEG 600 | 40 |   |
|   | Polysorbate 20 | 10 |   |
|   | Labrasol ® | 20 |   |
| 10 | Labrasol ® | 15 | 103.2 |
|   | Kolliphor ® RH40 | 30 |   |
|   | PEG 600 | 43 |   |
|   | Polysorbate 20 | 12 |   |
| 11 | Kolliphor ® RH40 | 40 | 102.9 |
|   | PEG 600 | 48 |   |
|   | Polysorbate 20 | 10 |   |
|   | Transcutol ® HP | 2 |   |
| 12 | Kolliphor ® RH40 | 40 | 79.7 |
|   | PEG 600 | 48 |   |
|   | Polysorbate 20 | 10 |   |
|   | Transcutol ® HP | 2 |   |
| 13 | Propylene glycol | 20 | 83.5 |
|   | Kolliphor ® RH40 | 40 |   |
|   | PEG 600 | 25 |   |
|   | Polysorbate 20 | 10 |   |
|   | Transcutol ® HP | 5 |   |
| 14 | Kolliphor ® RH40 | 40 | 90.5 |
|   | PEG 600 | 45 |   |
|   | Polysorbate 20 | 10 |   |
|   | Transcutol ® HP | 5 |   |
| 15 | Vitamin E TPGS | 40 | 44.2 |
|   | PEG 600 | 50 |   |
|   | Polysorbate 20 | 10 |   |
| 16 | Kolliphor ® RH40 | 40 | 81.2 |
|   | PEG 600 | 30 |   |
|   | Polysorbate 20 | 10 |   |
|   | Capryol ® 90 | 20 |   |
| 17 | Kolliphor ® RH40 | 40 | 97.5 |
|   | PEG 600 | 40 |   |
|   | Polysorbate 20 | 10 |   |
|   | Capryol ® 90 | 10 |   |
| 18 | Vitamin E TPGS | 40 | 68.5 |
|   | PEG 600 | 40 |   |
|   | Polysorbate 20 | 10 |   |
|   | Capmul ® MCM EP | 10 |   |
| 19 | Vitamin E TPGS | 40 | 71.1 |
|   | PEG 600 | 40 |   |
|   | Polysorbate 20 | 10 |   |
|   | Capmul ® C8 EP | 10 |   |
| 20 | Vitamin E TPGS | 40 | 73.3 |
|   | PEG 600 | 40 |   |
|   | Polysorbate 20 | 10 |   |
|   | Capmul ® MCM | 10 |   |

Example 3: Dispersion Testing

The three exemplary formulations were prepared at concentrations approximately 1000 lower than the equilibrium concentrations observed in the solubility assay of Example 2 to ensure that the compound of Formula (I) does not precipitate out during storage.

To prepare the bulk formulations, the excipients (according to the relative ratio of the excipients as shown in Table 4) were weighted in glass vials and agitated on a shaker at 50° C. to form homogeneous solutions. The compound of Formula (I) was then weighed into the excipient mixtures and placed at room temperature (Formulations A and B) or 50° C. (Formulation C). The resulting mixtures were protected from light and agitated until the compound of Formula (I) was completely dissolved. The composition of the formulations is summarized in Table 4:

TABLE 4

Exemplary Formulations

| Formulation | Excipients | Ratio w % | Formula (I) Concentration (mg/g) |
|---|---|---|---|
| A | Labrasol ® | 15 | 90 |
|   | Kolliphor ® RH40 | 30 |   |
|   | PEG 600 | 43 |   |
|   | Polysorbate 20 | 12 |   |

TABLE 4-continued

Exemplary Formulations

| Formulation | Excipients | Ratio w % | Formula (I) Concentration (mg/g) |
|---|---|---|---|
| B | Kolliphor® RH40 | 40 | 90 |
|   | PEG 600 | 40 |   |
|   | Polysorbate 20 | 10 |   |
|   | Capryol® 90 | 10 |   |
| C | Vitamin E TPGS | 40 | 60 |
|   | PEG 600 | 40 |   |
|   | Polysorbate 20 | 10 |   |
|   | Capmul® MCM | 10 |   |

Formulations A and B required more than 24 hours for full dissolution, while Formulation C was fully dissolved within 8 hours. Formulations A and B were dark red, viscous solutions, while Formulation C was a semi-solid solution.

Example 4: Dispersion and Characterization

The three exemplary formulations of Example 3 and the 60:40 Labrasol®/PEG400 formulation (40 mg/mL) were tested for dispersity in simulated gastric/intestinal fluids. Simulated gastric fluid (FaSSGF) (pH 1.6) and fasted state simulated intenstinal fluid (FaSSIF) (pH 6.5) were prepared using FaSSIF/FeSSIF/FaSSGF powder according to the manufacturer's instructions.

The bulk formulations (0.3 g Formulation A, 0.3 g Formulation B, 0.4 g Formulation C, 0.6 g Labrasol®/PEG400 formulation) were dispersed in 5 mL of FaSSGF (pH 1.6) to form the Stage 1 dispersions. The Stage 1 dispersions were further diluted using FaSSIF (pH 6.5) at a 1:1 ratio (v/v) to form the Stage 2 dispersions, which were subsequently diluted in one more volume of FaSSIF to form the Stage 3 dispersions. Dispersions from each stage were evaluated for droplet size by Malvern Nano Series, visual inspection, and microscopy. The dispersions were further diluted in DI water for droplet size determination by dynamic light scattering (DLS). The results of the droplet size and dispersion studies are summarized in Table 5:

TABLE 5

Formulations Droplet Size by DLS

|   | Stage 1 | | Stage 2 | | Stage 3 | |
|---|---|---|---|---|---|---|
| Formulation | Size (nm) | PdI | Size (nm) | PdI | Size (nm) | PdI |
| A (90 mg/g) | 123 | 0.22 | 121 | 0.24 | 120 | 0.22 |
| B (90 mg/g) | 112 | 0.23 | 126 | 0.38 | 110 | 0.26 |
| C (60 mg/g) | 25 | 0.21 | 23 | 0.18 | 19 | 0.15 |
| Labrasol®/PEG400 (40 mg/g) | 3024 | 0.60 | 2976 | 0.39 | 680 | 0.87 |

PdI = polydispersity index

The droplet size of Formulation A and Formulation B ranged from 110 nm to 130 nm with polydispersity indexes (PdI) of 0.2 or 0.3, while Formulation C had a smaller droplet size of approximately 20 nm. In contrast, the Labrasol®/PEG400 formulation displayed large and inhomogeneous droplet size and distribution.

Following dispersion, Formulation A, Formulation B, and the Labrasol®/PEG400 formulation were white opaque emulsions, while Formulation C was a clear solution, e.g., due to its small droplet size. After sitting without agitation for 30 minutes, the Labrasol®/PEG400 formulation coalesced on the bottoms of the vials, while the exemplary formulations remained as emulsions. After 2 hours, Formulation B flocculated.

Immediately following dispersion, the dispersions were analyzed by microscopy. Uniform droplets were observed for Formulation A and Formulation B for all three stages of dispersion. No droplets were observed in Formulation C, e.g., due to the small droplet size. The Labrasol®/PEG400 formulation dispersions displayed diverse droplet size, matching the observation from the dynamic light scattering measurement.

Figure 2:
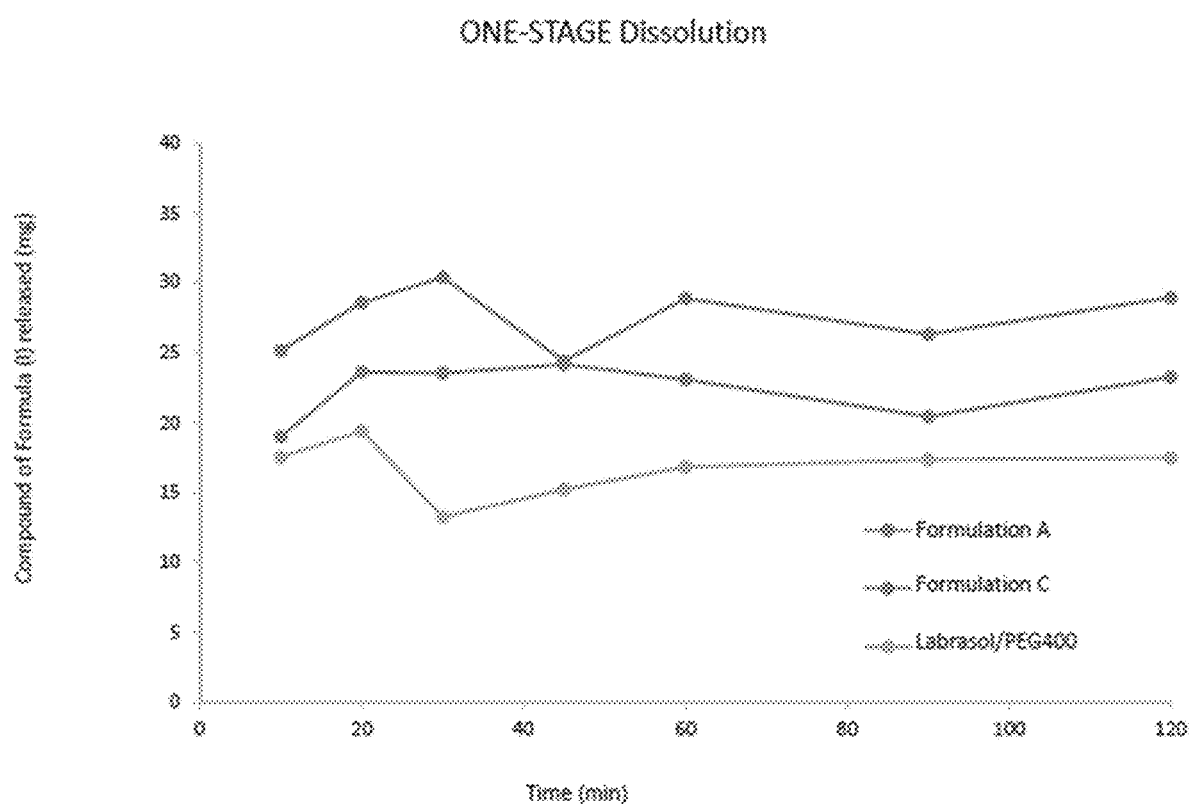
FIG. 2 shows the one-stage dissolution profiles of various formulations of a compound of Formula (I).
Figure 3:
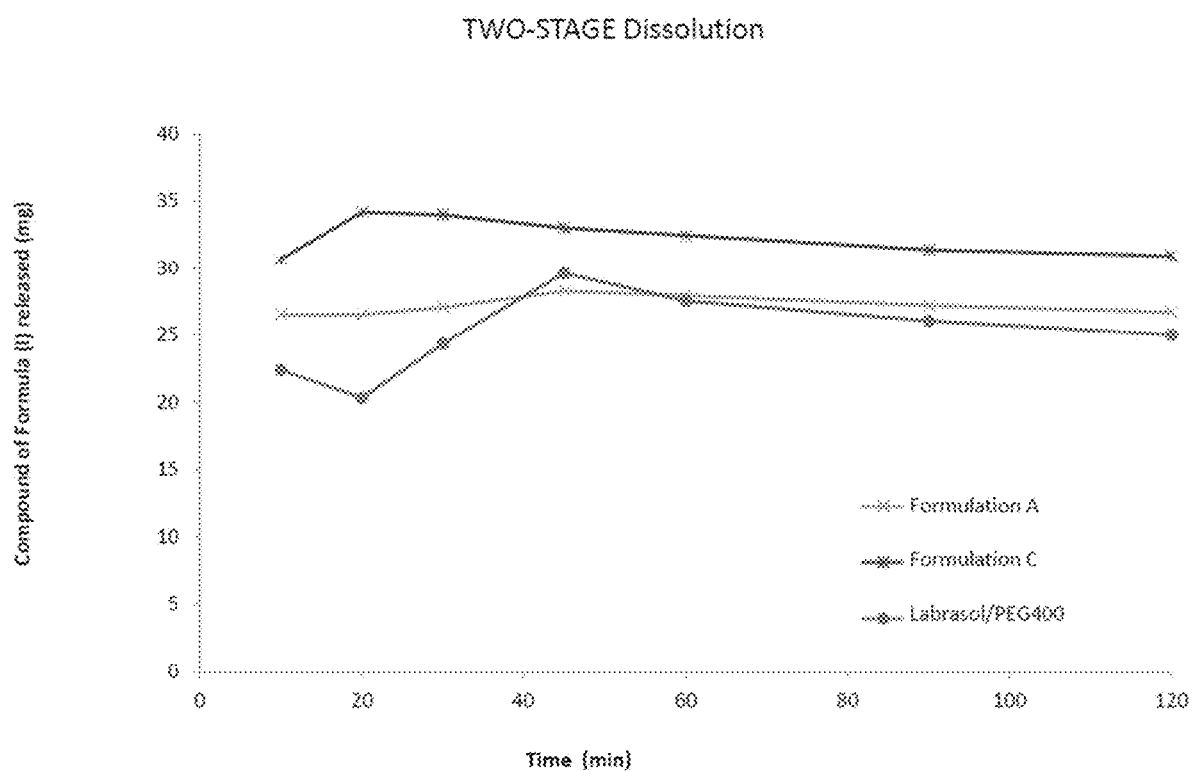
FIG. 3 shows the two-stage dissolution profiles of various formulations of a compound of Formula (I).

Dissolution profiles in simulated GI fluids were also analyzed, with Formulations A and C both showing comparable (e.g., about 80-120%, about 90-110%, or the like) or improved release in simulated GI fluid systems relative to Labrasol®/PEG400 formulation, as shown in FIG. 2 and FIG. 3.

Example 5: Stability Testing

Studies have shown that the compound of Formula (I) is susceptible to oxidation. Stability was analyzed using a variety of antioxidants. A bulk formulation containing Kolliphor® RH 40, PEG600, Polysorbate 80, Labrasol®, and Transcutol® HP (45:15:10:20:10 by weight) was prepared with a compound of Formula (I) concentration of 60 mg/g. Antioxidants, including Vitamin E (0.05 wt %), ascorbyl palmitate (0.05 wt %), butylated hydroxytoluene (0.005 wt %), and triethyl citrate (0.7 wt %) were dissolved/dispersed in the bulk formulation, respectively. The resulting samples were placed at room temperature in glass vials and protected from light. The samples were monitored for purity by HPLC at 0, 3, and 8 weeks. The results of the stability study are summarized in Table 6:

TABLE 6

Stability Test

| Antioxidants | 0 Weeks API Purity Area (%) | 3 Weeks API Purity Area (%) | 8 Weeks API Purity Area (%) |
|---|---|---|---|
| Without antioxidant | 99.05 | 79.93 | 87.15 |
| Vitamin E | 98.95 | 80.14 | 89.48 |
| Ascorbyl palmitate | 98.80 | 83.65 | 90.59 |
| Butylated hydroxytoluene | 98.96 | 81.08 | 88.76 |
| Triethyl citrate | 98.51 | 80.58 | 88.82 |

0.05 wt % ascorbyl palmitate showed the best antioxidant effect compared to the other antioxidants tested.

To confirm the effectiveness of antioxidants, Formulation A and Formulation C at 90 mg/g and 60 mg/g, respectively, were prepared with or without 0.5 wt % citric acid. The resulting formulations were placed in a stability chamber at room temperature and 60% relative humidity, and purity was monitored over the course of 5 months. The Labrasol®/PEG400 formulation with 0.5 wt % citric acid was tested as a control. The results of this stability study are summarized in Table 7:

TABLE 7

Effectiveness of Antioxidant

| Formulations | 0 Months API Purity Area (%) | 2 Months API Purity Area (%) | 5 Months API Purity Area (%) |
|---|---|---|---|
| Labrasol ®/PEG400 + 0.5% Citric Acid | 95.3 | 96.1 | 99.6 |
| Formulation A + 0.5% Citric Acid | 90.7 | 92.6 | 98.3 |
| Formulation A | 76.6 | 84.6 | 83.6 |
| Formulation C + 0.5% Citric Acid | 92.8 | 96.9 | N/A |
| Formulation C | 89.3 | 91.4 | N/A |

After two months, purity of the compound of Formula (I) was significantly lower in samples without citric acid. For Formulation A with citric acid, the purity of the compound of Formula (I) was 92.600 versus 84.6% for the same bulk solution without citric acid. Citric acid showed a similar protective effect against oxidation in Formulation C as well. At 5 months, Formulation A with citric acid was 98.300 pure versus 83.6% without citric acid, confirming the viability of citric acid as an antioxidant to ensure the long-term stability of the compound of Formula (I).

Formulation D comprises a compound of Formula (I) dissolved at a concentration of 92 mg/g in a mixture of Kolliphor® RH 40 (PEG-40 hydrogenated castor oil), PEG600, Polysorbate 20, Labrasol®, and citric acid. An 80 mg dosage is accomplished by a 0.87 g fill in a size 00 capsule. The composition of Formulation D is shown in Table 8:

TABLE 8

Formulation D

| Component | % w/w | Amount per 80 mg capsule |
|---|---|---|
| Kolliphor ® RH 40 | 27.09 | 236 mg |
| PEG600 | 38.83 | 338 mg |
| Polysorbate 20 | 10.84 | 94 mg |
| Labrasol ® | 13.54 | 118 mg |
| Citric acid | 0.50 | 4 mg |
| Compound of Formula (I) | 9.20 | 80 mg |

Example 6: Stability Study

Stability of Formulation D was evaluated on the bulk formulation solution at 5° C. and 25° C. for 5 months. The results of the stability study are summarized in Table 9:

TABLE 9

5-Month Stability

| Temperature | API |
|---|---|
| 5° C. | 99.9% |
| 25° C. | 98.3% |

Example 7: Rat Pharmacokinetics (PK) Study

The pharmacokinetics of Formulation D and Labrasol®/PEG400 formulations were compared in a rat study. A single oral dose of 25 mg/kg of the compound of Formula (I) was administered in four groups. The dose volumes for Groups 1 to 4 were 10, 10, 10, and 3 mL/kg, respectively. Group 1 received the Labrasol®/PEG400 formulation neat (undiluted). Group 2 received the Labrasol®/PEG400 formulation diluted as a 1:9 oil-in-water dispersion. Group 3 received Formulation D diluted as a 1:9 oil-in-water dispersion. Group 4 received Formulation D diluted as a 1:2 oil-in-water dispersion. The design of the rat pharmacokinetics study is summarized in FIG. 4.

Blood samples were collected over a 48-hour period at pre-dose, 0.25-, 0.5-, 1-, 2-, 4-, 8-, 24-, and 48-hour intervals. Concentration of the compound of Formula (I) was determined via a validated LC/MS/MS assay. Non-compartmental pharmacokinetic parameters were calculated with Phoenix WinNonlin (v8.1). The comparative pharmacokinetic parameters thus obtained are summarized in Table 10:

TABLE 10

Summary of Comparative PK Parameters in the Rat After a 25 mg/kg Dose

| Formulation | Group 1 Labrasol ®/ PEG400 Group 1 | Group 2 Labrasol ®/ PEG400 Group 2 | Group 3 D Group 3 | Group 4 D Group 4 |
|---|---|---|---|---|
| Dilution | neat | 1:9 | 1:9 | 1:2 |
| Volume | 10 | 10 | 10 | 3 |
| Dose (mg/kg) | 24.4 | 20.4 | 25.7 | 26.3 |
| $T_{max}$ (h) | 8 | 4 | 1 | 1 |
| $C_{max}$ (ng/mL) | 5,560 | 7,340 | 11,200 | 16,700 |
| $C_{max\_D}$ (kg*ng/mL/mg) | 228 | 360 | 436 | 635 |
| $AUC_{last}$ (h*ng/mL) | 115,000 | 75,600 | 129,000 | 121,000 |
| $AUC_{\infty}\_D\_obs$ (h*kg*ng/mL/mg) | 4750 | 3790 | 5070 | 4610 |
| Plasma half-life (h) | 6.11 | 7.89 | 6.94 | 5.12 |

Both neat and oil-in-water dispersion preparations of the Labrasol®/PEG400 formulation displayed slower rates of oral absorption compared to Formulation D preparations, as evidenced by the greater $T_{max}$ values observed for Groups 1 and 2 (8 and 4 hours, respectively, versus 1 hour). Both Formulation D preparations also resulted in higher $C_{max}$ values (11,200 and 16,700 ng/mL) compared to the Labrasol®/PEG400 groups (5,560 and 7,340 ng/mL). This 2-3 fold different is likely due to faster absorption by Formulation D.

The overall systemic exposure ($AUC_{last}$) of Formulation D preparations (129,000 and 121,000 h*ng/mL) were comparable (e.g., about 8010, about 90-110% o, or the like) to the neat Labrasol®/PEG400 formulation (115,000 h*ng/mL). The oil-in-water dispersion preparation of the Labrasol®/PEG400 formulation resulted in the lowest systemic exposure (75,600 h*ng/mL). When AUC was normalized by dose for 0 to infinity ($AUC_\infty\_D\_obs$), Groups 1, 3, and 4 values were comparable (e.g., about 80-120%, about 90-110%, or the like) at 4,754; 5,070; and 4,610 h*kg*ng/mL/mg, respectively. Only the oil-in-water dispersion preparation of the Labrasol®/PEG400 formulation resulted in a lesser value (3,790 h*kg*ng/mL/mg).

The different dispersion ratios and dose volumes of the two Formulation D preparations (3 mL for 1:2 and 10 mL for 1:9) did not result in differences in systemic exposure, as evidenced by similar $AUC_{last}$ values. Thus, the higher $C_{max}$ value of the 1:2 preparation versus the 1:9 Formulation D preparation appears to be attributable to the rates of absorption, not to differences in systemic exposure. This observation is further confirmed by the comparable (e.g., about 8010, about 90-110%, or the like) $AUC_\infty\_D\_obs$ values (5,070 vs. 4,610 h*kg*ng/mL/mg) for the 1:9 and 1:2 preparations, respectively.

The neat Labrasol®/PEG400 formulation preparation showed comparable (e.g., about 80-120%, about 90-110%, or the like) total systemic exposure ($AUC_{last}$) and dose-normalized AUC ($AUC_\infty\_D\_obs$) to both Formulation D preparations. The 1:9 Labrasol®/PEG400 formulation preparation has markedly lower $AUC_{last}$ and $AUC_\infty\_D\_obs$ values but higher $C_{max}$ and $C_{max}\_D$ values compared to the neat preparation. The 1:9 preparation also displayed the longest plasma elimination half-life (7.89 hours). When taken together, these parameters indicate that the 1:9 preparation has an altered absorption profile compared to the neat preparation. This difference in absorption profile impacted total exposure and may have been responsible for delayed elimination.

Both Formulation D preparations showed comparable (e.g., about 80-120%, about 90-110%, or the like) total system exposure (AUC) and plasma half-life to the neat Labrasol®/PEG400 formulation preparation. The Formulation D resulted in an increased rate of absorption, with a decreased $T_{max}$ and an increased $C_{max}$ relative to the Labrasol®/PEG400 formulation.

Example 8: Human Pharmacokinetic (PK) Study (2-Component)

Pharmacokinetic data obtained for 13 human subjects treated with the two-component formulation system of Example 1 is summarized herein. Subjects 1, 4, 6, and 7 were enrolled in Cohort 1 (3.2 mg/kg/day); Subjects 8, 9, and 10 were enrolled in Cohort 2 (6.4 mg/kg/day); and Subjects 11, 12, 15, 16, 19, and 20 were enrolled in Cohort 3 (12.8 mg/kg/day). The plasma samples from the first BID dose on Cycle 1/Day 1 were analyzed for all 13 subjects. The dosage levels were achieved with BID dosing. Thus, for Cohort 1, 3.2 mg/kg/day was 1.6 mg/kg BID; for Cohort 2, 6.4 mg/kg/day was 3.2 mg/kg BID; and for Cohort 3, 12.8 mg/kg/day was 6.4 mg/kg BID.

The individual pharmacokinetic parameters by cohort for the 12-hour time course of a single dose by subject are summarized in FIG. 5.

Individuals in Cohort 1 (1.6 mg/kg BID) demonstrated a $T_{max}$ that ranged from 0.82 to 4 hours and a $C_{max}$ that ranged from 735 to 1,380 ng/mL. The $C_{max}$ normalized by dose ($C_{max}\_D$) ranged from 4.9 to 9.2 ng/mL/mg. The $AUC_{last}$ ranged from 5,430 to 7,640 h*ng/mL. When normalized by dose, the $AUC_{last}\_D$ ranged from 30.1 to 43.8 h*ng/mL/mg.

Individuals in Cohort 2 (3.2 mg/kg BID) demonstrated a $T_{max}$ that ranged from 1.1 to 2 hours and a $C_{max}$ that ranged from 1,910 to 3,260 ng/mL. The $C_{max}$ normalized by dose ($C_{max}\_D$) ranged from 6.2 to 12.1 ng/mL/mg. The $AUC_{last}$ ranged from 11,700 to 19,800 h*ng/mL. When normalized by dose, the $AUC_{last}\_D$ ranged from 32.5 to 73.3 h*ng/mL/mg.

Individuals in Cohort 3 (6.4 mg/kg BID) demonstrated a $T_{max}$ that ranged from 1 to 6.1 hours and a $C_{max}$ that ranged from 2,220 to 3,730 ng/mL. The $C_{max}$ normalized by dose ($C_{max}\_D$) ranged from 4.91 to 7.77 ng/mL/mg. The $AUC_{last}$ ranged from 12,700 to 29,200 h*ng/mL. When normalized by dose, the $AUC_{last}\_D$ ranged from 28.2 to 60.8 h*ng/mL/mg.

The mean pharmacokinetic parameters by cohort for the 12-hour time course of a single dose are summarized in FIG. 6.

Cohort 1 demonstrated mean values for $T_{max}$, $C_{max}$, $C_{max}\_D$, $AUC_{last}$, and $AUC_{last}\_D$ of 1.91 hours, 1,090 ng/mL, 6.33 ng/mL/mg, 6,360 h*ng/mL, and 36.9 h*ng/mL/mg, respectively.

Cohort 2 demonstrated mean values for $T_{max}$, $C_{max}$, $C_{max}\_D$, $AUC_{last}$, and $AUC_{last}\_D$ of 1.39 hours, 2,460 ng/mL, 8.73 ng/mL/mg, 14,800 h*ng/mL, and 53 h*ng/mL/mg, respectively.

Cohort 3 demonstrated mean values for $T_{max}$, $C_{max}$, $C_{max}\_D$, $AUC_{last}$, and $AUC_{last}\_D$ of 2.74 hours, 2,690 ng/mL, 5.81 ng/mL/mg, 19,200 h*ng/mL, and 41.7 h*ng/mL/mg, respectively.

Example 9: Spray Dried Dispersion (SDD) and Nanosuspension Formulations

A spray dried dispersion (SDD) formulation of the compound of Formula (I) was prepared as follows. A spray dried dispersion of the compound of Formula (I) in EUDRAGIT® E PO (375 mg, 20% drug loading) was suspended in 0.5% hydroxypropyl methylcellulose (HPMC) 603/0.2% Tween 80 solution (30 mL) with 30 seconds of shaking followed by 15 minutes of stirring with a magnetic stir bar. The resulting suspension was shaken gently for 15 seconds prior to dosing.

A nanosuspension of the compound of Formula (I) was prepared as follows. A nanosuspension of the compound of Formula (I) in 1% Tween80 (1.0 mL, 101.37 mg/mL) was vortexed for 15-20 seconds and then transfer to USP water (39.5 mL). The resulting suspension was vortexed for 15-20 seconds prior to dosing.

Figure 7:
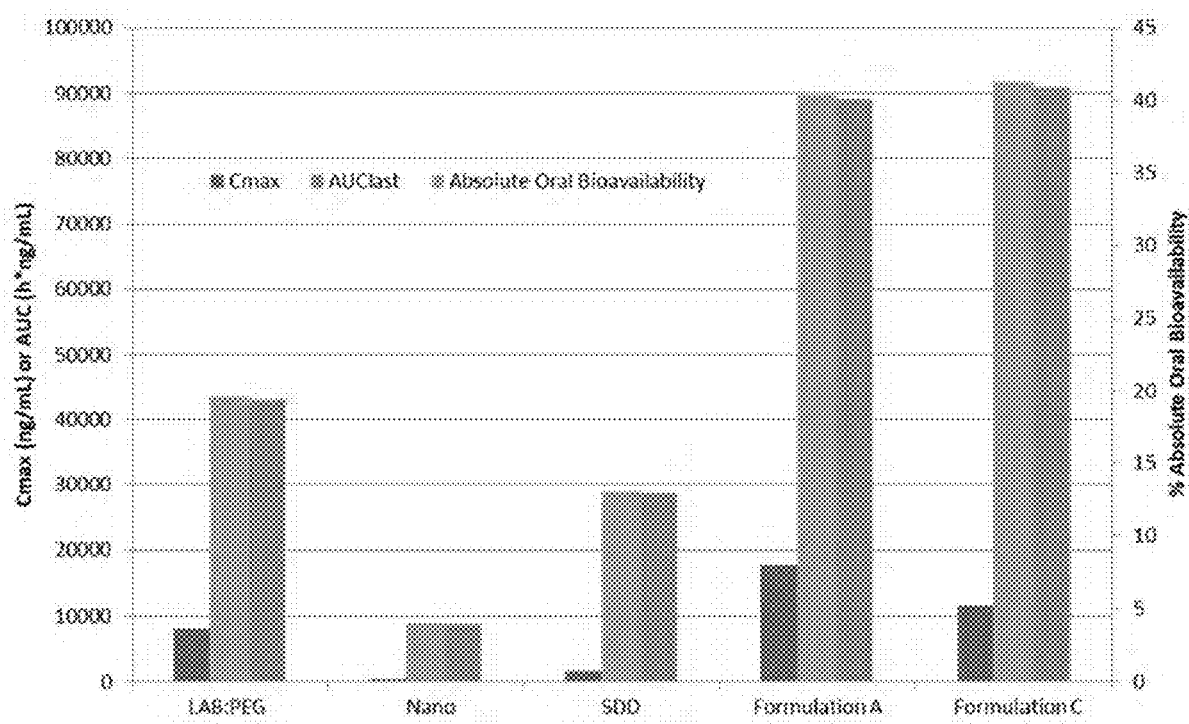
FIG. 7 shows the results of pharmacokinetics analyses for various formulations of compounds of Formula (I).

When subjected to a rat pharmacokinetics study, the spray dried dispersion and the nanosuspension gave results as shown in FIG. 7. As demonstrated, not only were the nanosuspension and the SDD formulation significantly inferior to the multi-component formulations provided herein, but were also inferior to the 2-component (Labrasol®/PEG400) formulation as well in $C_{max}$ and AUC.

Example 10: Human Bioavailability and Pharmacokinetic (PK) Study Comparing 2-Component Formulation and Self-Emulsifying-Drug-Dispersion (SEDD) Formulation A total of 14 subjects diagnosed with advanced cancers were administered the compound of Formula (I) dosed at 12.8 mg/kg/day using the two-component (Labrasol®/PEG400) formulation system of Example 1 (8 subjects) or at 12.8 mg/kg/day using the SEDD formulation described in Examples 1 and 5 (6 subjects). Plasma concentrations of a compound of Formula (I) were used for the evaluation of oral bioavailability and pharmacokinetics.

Blood Collection: PK sampling was performed at the following time points for Cycle 1/Day 1 (C1/D1): pre-dose, 1, 2, 4, 6, 8, 11:59 hr Post $1^{st}$ dose (before $2^{nd}$ dose) and at 23:59 hr Post $1^{st}$ dose (before $3^{rd}$ dose). Variability in timepoints was allowed at ±15 minutes for the 1, 2, and 4 hr time points and ±30 minutes for the 6, 8, 12 and 24 hr time points.

Results

Figure 8:
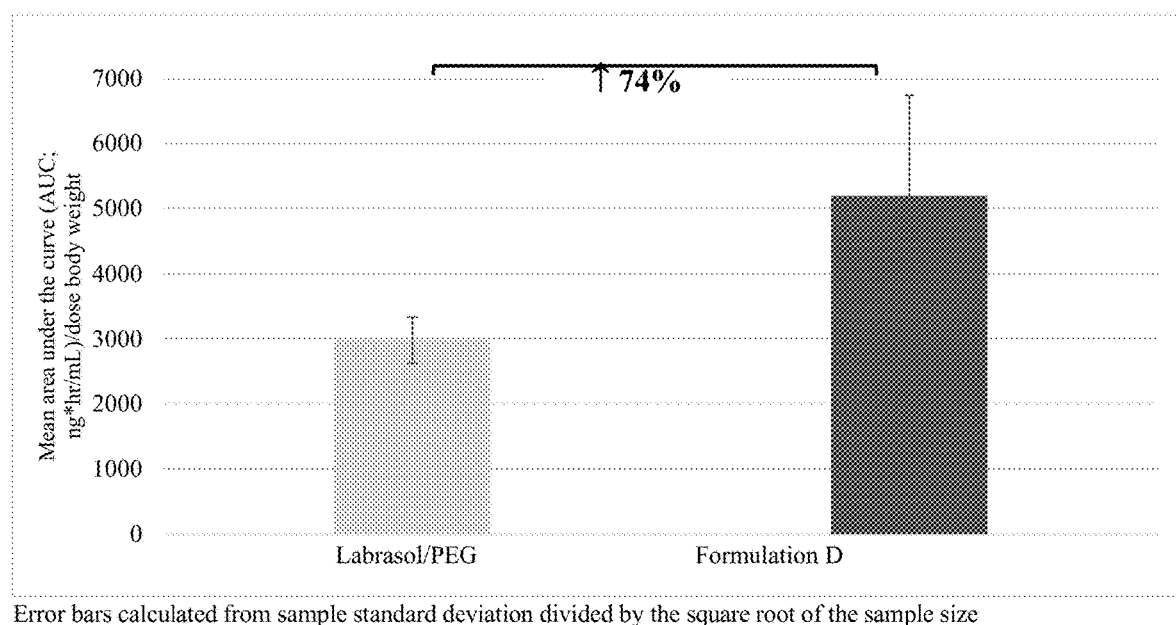
FIG. 8 shows the mean area under the curve per dose body weight for various formulations of a compound of Formula (I).

Human PK Data Through the 12-Hour Time Point:

The plasma samples from the first BID dose (6.4 mg/kg) on Cycle 1/Day 1 were analyzed for all 14 subjects. The mean area under the curve (AUC), controlling dose and body weight was 2,982 ng*hr/mL in the cohort using the Labrasol®/PEG formulation and 5,198 ng*hr/mL in the cohort using Formulation D. This resulted in a 74% increase in plasma drug exposure among the cohort using Formulation D as shown in FIG. 8.

Safety:

In addition to improved AUC, the SEDD formulation (Formulation D) has demonstrated an improved safety profile. Four of the 8 subjects in the cohort using the Labrasol®/PEG formulation reported adverse events (AEs) deemed attributable to the drug in the Labrasol/PEG formulation, including 3 Grade 3 events.

No subjects in the cohort using Formulation D reported any events attributable to the drug dosed in the SEDD formulation as outlined in Table 11:

TABLE 11

Safety Analysis of Subjects Dosed at 12.8 mg/kg/day

| Formulation/Type of Adverse Events | Number of reported AE | Number of subjects reporting AE |
|---|---|---|
| Labrasol/PEG Formulation Dose (n = 8) Constitutional** | 19 | 4 |
| Grade 1 | 3 | |
| Grade 2 | 3 | |
| Gastrointestinal | | |
| Grade 1 | 5 | |
| Grade 2 | 5 | |
| Grade 3 | 3 | |
| Formulation D Dose (n = 6) | 0 | 0 |

* Safety analysis based on 14 subjects treated at dose of 12.8 mg/kg/day.
**Constitutional includes fatigue, appetite changes, and weight loss.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

The invention claimed is:

1. An improved method of administering a compound of Formula (I):

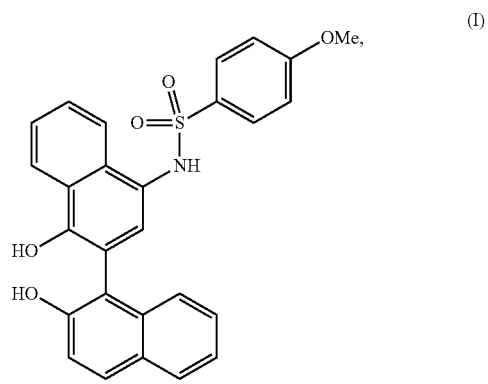 [SMILES: COc1ccc(S(=O)(=O)Nc2cc(-c3c(O)ccc4ccccc34)c(O)c3ccccc23)cc1]

or a pharmaceutically acceptable salt thereof, in a subject in need thereof, wherein the improvement comprises administering to the subject a pharmaceutical composition comprising:
   i) the compound of Formula (I), or a pharmaceutically acceptable salt thereof;
   ii) a glyceride emulsifier, wherein the weight ratio of the compound of Formula (I) to the glyceride emulsifier is about 1:1 to about 1:2;
   iii) a solubilizer, wherein the weight ratio of the compound of Formula (I) to the solubilizer is about 1:2 to about 1:4;
   iv) a polyethylene glycol (PEG), wherein the weight ratio of the compound of Formula (I) to the PEG is about 1:3 to about 1:5;
   v) a surfactant, wherein the weight ratio of the compound of Formula (I) to the surfactant is about 1:1 to about 1:2; and
   vi) an antioxidant, wherein the weight ratio of the compound of Formula (I) to the antioxidant is about 15:1 to about 25:1.

2. The method of claim 1, wherein the improvement reduces pill burden for the compound of Formula (I) by at least 2-fold than when a pharmaceutical composition consisting essentially of the compound of Formula (I), a glyceride emulsifier, and PEG, wherein the glyceride emulsifier and the PEG in the composition consisting essentially of the compound of Formula (I), glyceride emulsifier, and PEG are in a weight ratio of about 60:40, is administered to the subject.

3. The method of claim 1, wherein the improvement provides a greater $C_{max}$ of the compound of formula (I) than when a pharmaceutical composition consisting essentially of the compound of Formula (I), a glyceride emulsifier, and PEG, wherein the glyceride emulsifier and the PEG in the composition consisting essentially of the compound of Formula (I), glyceride emulsifier, and PEG are in a weight ratio of about 60:40, is administered to the subject.

4. The method of claim 3, wherein the improvement provides a $C_{max}$ that is at least 1.3 times greater than when a pharmaceutical composition consisting essentially of the compound of Formula (I), a glyceride emulsifier, and PEG, wherein the glyceride emulsifier and the PEG in the composition consisting essentially of the compound of Formula (I), glyceride emulsifier, and PEG are in a weight ratio of about 60:40, is administered to the subject.

5. The method of claim 1, wherein the improvement provides a greater area under the curve from time 0 extrapolated to infinite time ($AUC_{0\to\infty}$) of the compound of formula (I) than when a pharmaceutical composition consisting essentially of the compound of Formula (I), a glyceride emulsifier, and PEG, wherein the glyceride emulsifier and the PEG in the composition consisting essentially of the compound of Formula (I), glyceride emulsifier, and PEG are in a weight ratio of about 60:40, is administered to the subject.

6. The method of claim 5, wherein the improvement provides an $AUC_{0\to\infty}$ that is at least 1.3 times greater than when a pharmaceutical composition consisting essentially of the compound of Formula (I), a glyceride emulsifier, and PEG, wherein the glyceride emulsifier and the PEG in the composition consisting essentially of the compound of Formula (I), glyceride emulsifier, and PEG are in a weight ratio of about 60:40, is administered to the subject.

7. The method of claim 1, wherein the weight ratio of the compound of Formula (I) to the glyceride emulsifier is about 1:1.

8. The method of claim 1, wherein the weight ratio of the compound of Formula (I) to the solubilizer is about 1:3.

9. The method of claim 1, wherein the weight ratio of the compound of Formula (I) to the PEG is about 1:4.

10. The method of claim 1, wherein the weight ratio of the compound of Formula (I) to the surfactant is about 1:1.

11. The method of claim 1, wherein the weight ratio of the compound of Formula (I) to the antioxidant is about 20:1.

12. The method of claim 7, wherein the pharmaceutical composition comprises at least 50 mg of the compound of formula (I).

13. The method of claim 1, wherein the solubilizer is polyoxyl castor oil.

14. The method of claim 1, wherein the PEG has an average molecular weight of about 200 to about 1000 Da.

15. The method of claim 1, wherein the surfactant is polysorbate.

16. The method of claim 1, wherein at least 50 mg of the glyceride emulsifier, at least 100 mg of the solubilizer, at least 150 mg PEG, at least 50 mg of surfactant, and at least 2 mg of the antioxidant are present in the pharmaceutical composition.

17. The method of claim 1, wherein the subject has cancer, fibrosis, or chronic inflammation.

18. The method of claim 17, wherein the subject has cancer and the cancer is head and neck cancer, lung cancer, liver cancer, breast cancer, ovarian cancer, colon cancer, multiple myeloma, prostate cancer, cervical cancer, brain cancer, pancreatic cancer, myelodysplastic syndrome, leukemia, lymphoma, neuroblastoma, kidney cancer, or metastatic melanoma.

19. The method of claim 17, wherein the subject has fibrosis and the fibrosis is associated with pulmonary fibrosis, intestine fibrosis, pancreatic fibrosis, joint fibrosis, liver fibrosis, retroperitoneal fibrosis, myelofibrosis, dermal fibrosis, non-alcoholic fatty liver disease, steatohepatitis, or systemic sclerosis.

20. The method of claim 17, wherein the subject has chronic inflammation.

* * * * *

UNITED STATES PATENT AND TRADEMARK OFFICE
CERTIFICATE OF CORRECTION

PATENT NO. : 12,053,444 B2
APPLICATION NO. : 18/059270
DATED : August 6, 2024
INVENTOR(S) : Imran Alibhai et al.

Page 1 of 1

It is certified that error appears in the above-identified patent and that said Letters Patent is hereby corrected as shown below:

In the Claims

At Column 52, Claim number 12, Line number 3, please delete "The method of claim 7, wherein the pharmaceutical" and replace with --The method of claim 1, wherein the pharmaceutical--

Signed and Sealed this
Tenth Day of September, 2024

Katherine Kelly Vidal
*Director of the United States Patent and Trademark Office*